(12) United States Patent
Stefanchik et al.

(10) Patent No.: US 8,075,572 B2
(45) Date of Patent: Dec. 13, 2011

(54) SURGICAL SUTURING APPARATUS

(75) Inventors: David Stefanchik, Morrow, OH (US); David B. Griffith, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1197 days.

(21) Appl. No.: 11/796,035

(22) Filed: Apr. 26, 2007

(65) Prior Publication Data

US 2008/0269782 A1    Oct. 30, 2008

(51) Int. Cl.
*A61B 17/04* (2006.01)
(52) U.S. Cl. .................................. 606/144; 606/139
(58) Field of Classification Search .................. 606/139, 606/144, 145, 148
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |

(Continued)

FOREIGN PATENT DOCUMENTS

AU    666310 B2    2/1996

(Continued)

OTHER PUBLICATIONS

International Search Report for PCT/US2008/061359, Apr. 27, 2009. (7 pages).

(Continued)

*Primary Examiner* — Darwin Erezo

(57) ABSTRACT

A surgical suturing apparatus is described. The suturing apparatus has a needle having at least one pointed end, a channel for releasably receiving the needle, a needle positioning assembly having members for moving the needle and an actuation assembly for actuating the needle positioning assembly. The needle includes a first puncturing point at a proximal end thereof and an engagement section adjacent thereto, a distal end, which may have a second puncturing point, and another engagement section adjacent the distal end. A structure, such as an eye or a slot, is provided to secure a length of suture material to the needle. The members for moving the needle include an engagement member for releasably engaging one of the engagement sections of the needle to effect axial movement of the needle within the channel, a ramp member for effecting movement of the needle in the distal direction along the longitudinal axis of the channel and for urging the proximal end of the needle out of the channel, and a snare axially movable within the channel and having a portion releasably housed within the channel. The snare portion is configured for capturing the proximal engagement section of the needle to guide the needle in a proximal direction when the needle is out of the channel and to guide the return of the needle to the channel.

28 Claims, 13 Drawing Sheets

U.S. PATENT DOCUMENTS

| | | | |
|---|---|---|---|
| 3,170,471 A | 2/1965 | Schnitzer | |
| 3,435,824 A | 4/1969 | Gamponia | |
| 3,470,876 A | 10/1969 | Barchilon | |
| 3,669,487 A | 6/1972 | Roberts et al. | |
| 3,746,881 A | 7/1973 | Fitch et al. | |
| 3,799,672 A | 3/1974 | Vurek | |
| 3,854,473 A | 12/1974 | Matsuo | |
| 3,946,740 A | 3/1976 | Bassett | |
| 3,948,251 A | 4/1976 | Hosono | |
| 3,994,301 A | 11/1976 | Agris | |
| 4,011,872 A | 3/1977 | Komiya | |
| 4,012,812 A | 3/1977 | Black | |
| 4,164,225 A | 8/1979 | Johnson et al. | |
| 4,178,920 A | 12/1979 | Cawood, Jr. et al. | |
| 4,207,873 A | 6/1980 | Kruy | |
| 4,235,238 A | 11/1980 | Ogiu et al. | |
| 4,258,716 A | 3/1981 | Sutherland | |
| 4,278,077 A | 7/1981 | Mizumoto | |
| 4,285,344 A | 8/1981 | Marshall | |
| 4,311,143 A | 1/1982 | Komiya | |
| 4,329,980 A | 5/1982 | Terada | |
| 4,396,021 A | 8/1983 | Baumgartner | |
| 4,452,246 A | 6/1984 | Bader et al. | |
| 4,461,281 A | 7/1984 | Carson | |
| 4,491,132 A | 1/1985 | Aikins | |
| 4,527,331 A | 7/1985 | Lasner et al. | |
| 4,527,564 A | 7/1985 | Eguchi et al. | |
| 4,538,594 A | 9/1985 | Boebel et al. | |
| D281,104 S | 10/1985 | Davison | |
| 4,569,347 A | 2/1986 | Frisbie | |
| 4,580,551 A | 4/1986 | Siegmund et al. | |
| 4,646,722 A | 3/1987 | Silverstein et al. | |
| 4,653,476 A | 3/1987 | Bonnet | |
| 4,669,470 A | 6/1987 | Brandfield | |
| 4,671,477 A | 6/1987 | Cullen | |
| 4,685,447 A | 8/1987 | Iversen et al. | |
| 4,711,240 A | 12/1987 | Goldwasser et al. | |
| 4,712,545 A | 12/1987 | Honkanen | |
| 4,721,116 A | 1/1988 | Schintgen et al. | |
| 4,733,662 A | 3/1988 | DeSatnick et al. | |
| D295,894 S | 5/1988 | Sharkany et al. | |
| 4,763,669 A | 8/1988 | Jaeger | |
| 4,770,188 A | 9/1988 | Chikama | |
| 4,815,450 A | 3/1989 | Patel | |
| 4,823,794 A | 4/1989 | Pierce | |
| 4,829,999 A | 5/1989 | Auth | |
| 4,873,979 A | 10/1989 | Hanna | |
| 4,880,015 A | 11/1989 | Nierman | |
| 4,911,148 A | 3/1990 | Sosnowski et al. | |
| 4,926,860 A | 5/1990 | Stice et al. | |
| 4,938,214 A | 7/1990 | Specht et al. | |
| 4,950,273 A | 8/1990 | Briggs | |
| 4,950,285 A | 8/1990 | Wilk | |
| 4,977,887 A | 12/1990 | Gouda | |
| 4,984,581 A | 1/1991 | Stice | |
| 5,007,917 A | 4/1991 | Evans | |
| 5,010,876 A | 4/1991 | Henley et al. | |
| 5,020,514 A | 6/1991 | Heckele | |
| 5,020,535 A | 6/1991 | Parker et al. | |
| 5,025,778 A | 6/1991 | Silverstein et al. | |
| 5,033,169 A | 7/1991 | Bindon | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,050,585 A | 9/1991 | Takahashi | |
| 5,052,372 A | 10/1991 | Shapiro | |
| 5,065,516 A | 11/1991 | Dulebohn | |
| 5,066,295 A | 11/1991 | Kozak et al. | |
| 5,123,913 A | 6/1992 | Wilk et al. | |
| 5,123,914 A | 6/1992 | Cope | |
| 5,133,727 A | 7/1992 | Bales et al. | |
| 5,147,374 A | 9/1992 | Fernandez | |
| 5,174,300 A | 12/1992 | Bales et al. | |
| 5,176,126 A | 1/1993 | Chikama | |
| 5,190,050 A | 3/1993 | Nitzsche | |
| 5,190,555 A | 3/1993 | Wetter et al. | |
| 5,192,284 A | 3/1993 | Pleatman | |
| 5,201,752 A | 4/1993 | Brown et al. | |
| 5,201,908 A | 4/1993 | Jones | |
| 5,203,785 A | 4/1993 | Slater | |
| 5,203,787 A | 4/1993 | Noblitt et al. | |
| 5,209,747 A | 5/1993 | Knoepfler | |
| 5,217,003 A | 6/1993 | Wilk | |
| 5,217,453 A | 6/1993 | Wilk | |
| 5,219,357 A | 6/1993 | Honkanen et al. | |
| 5,219,358 A | 6/1993 | Bendel et al. | |
| 5,222,362 A | 6/1993 | Maus et al. | |
| 5,222,965 A | 6/1993 | Haughton | |
| 5,234,453 A | 8/1993 | Smith et al. | |
| 5,235,964 A | 8/1993 | Abenaim | |
| 5,242,456 A | 9/1993 | Nash et al. | |
| 5,246,424 A | 9/1993 | Wilk | |
| 5,259,366 A | 11/1993 | Reydel et al. | |
| 5,263,958 A | 11/1993 | deGuillebon et al. | |
| 5,273,524 A | 12/1993 | Fox et al. | |
| 5,275,607 A | 1/1994 | Lo et al. | |
| 5,284,128 A | 2/1994 | Hart | |
| 5,284,162 A | 2/1994 | Wilk | |
| 5,287,845 A | 2/1994 | Faul et al. | |
| 5,290,299 A | 3/1994 | Fain et al. | |
| 5,290,302 A | 3/1994 | Pericic | |
| 5,295,977 A | 3/1994 | Cohen et al. | |
| 5,297,536 A | 3/1994 | Wilk | |
| 5,301,061 A | 4/1994 | Nakada et al. | |
| 5,312,333 A | 5/1994 | Churinetz et al. | |
| 5,312,351 A | 5/1994 | Gerrone | |
| 5,312,416 A | 5/1994 | Spaeth et al. | |
| 5,312,423 A * | 5/1994 | Rosenbluth et al. | 606/148 |
| 5,320,636 A | 6/1994 | Slater | |
| 5,325,845 A | 7/1994 | Adair | |
| 5,330,471 A | 7/1994 | Eggers | |
| 5,330,486 A | 7/1994 | Wilk | |
| 5,330,488 A | 7/1994 | Goldrath | |
| 5,330,496 A | 7/1994 | Alferness | |
| 5,330,502 A | 7/1994 | Hassler et al. | |
| 5,331,971 A | 7/1994 | Bales et al. | |
| 5,334,198 A | 8/1994 | Hart et al. | |
| 5,344,428 A | 9/1994 | Griffiths | |
| 5,350,391 A | 9/1994 | Iacovelli | |
| 5,352,184 A | 10/1994 | Goldberg et al. | |
| 5,352,222 A | 10/1994 | Rydell | |
| 5,354,302 A | 10/1994 | Ko | |
| 5,354,311 A | 10/1994 | Kambin et al. | |
| 5,356,408 A | 10/1994 | Rydell | |
| 5,364,408 A * | 11/1994 | Gordon | 606/144 |
| 5,364,410 A | 11/1994 | Failla et al. | |
| 5,366,466 A | 11/1994 | Christian et al. | |
| 5,366,467 A | 11/1994 | Lynch et al. | |
| 5,368,605 A | 11/1994 | Miller, Jr. | |
| 5,370,647 A | 12/1994 | Graber et al. | |
| 5,374,273 A | 12/1994 | Nakao et al. | |
| 5,374,275 A * | 12/1994 | Bradley et al. | 606/144 |
| 5,374,277 A | 12/1994 | Hassler | |
| 5,377,695 A | 1/1995 | An Haack | |
| 5,383,877 A | 1/1995 | Clarke | |
| 5,383,888 A | 1/1995 | Zvenyatsky et al. | |
| 5,391,174 A | 2/1995 | Weston | |
| 5,392,789 A | 2/1995 | Slater et al. | |
| 5,395,386 A | 3/1995 | Slater | |
| 5,401,248 A | 3/1995 | Bencini | |
| 5,403,328 A * | 4/1995 | Shallman | 606/144 |
| 5,403,342 A | 4/1995 | Tovey et al. | |
| 5,403,348 A | 4/1995 | Bonutti | |
| 5,405,073 A | 4/1995 | Porter | |
| 5,405,359 A | 4/1995 | Pierce | |
| 5,409,478 A | 4/1995 | Gerry et al. | |
| 5,417,699 A * | 5/1995 | Klein et al. | 606/144 |
| 5,423,821 A | 6/1995 | Pasque | |
| 5,433,721 A | 7/1995 | Hooven et al. | |
| 5,439,471 A | 8/1995 | Kerr | |
| 5,439,478 A | 8/1995 | Palmer | |
| 5,441,059 A | 8/1995 | Dannan | |
| 5,441,499 A | 8/1995 | Fritzsch | |
| 5,449,021 A | 9/1995 | Chikama | |
| 5,456,667 A | 10/1995 | Ham et al. | |
| 5,456,684 A | 10/1995 | Schmidt et al. | |
| 5,458,131 A | 10/1995 | Wilk | |

| | | |
|---|---|---|
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A * | 10/1995 | Voda ............................ 606/144 |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A * | 3/1996 | Riza ............................ 606/148 |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A * | 6/1996 | Hinchliffe .................. 606/144 |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A * | 11/1996 | Yoon ............................ 606/139 |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A * | 1/1997 | Edelstein .................... 606/144 |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A * | 3/1997 | Christy ........................ 606/144 |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,628,732 A | 5/1997 | Antoon, Jr. et al. |
| 5,630,782 A | 5/1997 | Adair |
| 5,643,283 A | 7/1997 | Younker |
| 5,643,292 A * | 7/1997 | Hart ............................ 606/144 |
| 5,643,294 A | 7/1997 | Tovey et al. |
| 5,644,798 A | 7/1997 | Shah |
| 5,645,083 A | 7/1997 | Essig et al. |
| 5,649,372 A | 7/1997 | Souza |
| 5,653,677 A | 8/1997 | Okada et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,741,278 A | 4/1998 | Stevens |
| 5,741,285 A | 4/1998 | McBrayer et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A * | 9/1998 | Kontos ........................ 606/144 |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,849,022 A | 12/1998 | Sakashita et al. |
| 5,853,374 A | 12/1998 | Hart et al. |
| 5,855,585 A * | 1/1999 | Kontos ........................ 606/144 |
| 5,860,913 A | 1/1999 | Yamaya et al. |
| 5,860,995 A | 1/1999 | Berkelaar |
| 5,868,762 A * | 2/1999 | Cragg et al. .................. 606/144 |
| 5,876,411 A * | 3/1999 | Kontos ........................ 606/144 |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A * | 7/1999 | Kontos ........................ 606/213 |
| 5,936,536 A | 8/1999 | Morris |
| 5,944,718 A | 8/1999 | Austin et al. |
| 5,951,549 A | 9/1999 | Richardson et al. |
| 5,954,720 A | 9/1999 | Wilson et al. |
| 5,954,731 A | 9/1999 | Yoon |
| 5,957,943 A | 9/1999 | Vaitekunas |
| 5,957,953 A | 9/1999 | DiPoto et al. |
| 5,971,995 A | 10/1999 | Rousseau |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A * | 11/1999 | Kontos ........................ 606/148 |
| 5,980,556 A | 11/1999 | Giordano et al. |
| 5,984,938 A | 11/1999 | Yoon |

| | | | |
|---|---|---|---|
| 5,989,182 A | 11/1999 | Hori et al. | |
| 5,993,447 A | 11/1999 | Blewett et al. | |
| 5,997,555 A * | 12/1999 | Kontos ................ 606/148 | |
| 6,001,120 A | 12/1999 | Levin | |
| 6,004,330 A | 12/1999 | Middleman et al. | |
| 6,007,566 A | 12/1999 | Wenstrom, Jr. | |
| 6,010,515 A | 1/2000 | Swain et al. | |
| 6,012,494 A | 1/2000 | Balazs | |
| 6,019,770 A | 2/2000 | Christoudias | |
| 6,024,708 A | 2/2000 | Bales et al. | |
| 6,024,747 A * | 2/2000 | Kontos ................ 606/144 | |
| 6,027,522 A | 2/2000 | Palmer | |
| 6,030,365 A | 2/2000 | Laufer | |
| 6,033,399 A | 3/2000 | Gines | |
| 6,053,927 A | 4/2000 | Hamas | |
| 6,066,160 A | 5/2000 | Colvin et al. | |
| 6,068,603 A | 5/2000 | Suzuki | |
| 6,068,629 A | 5/2000 | Haissaguerre et al. | |
| 6,071,233 A | 6/2000 | Ishikawa et al. | |
| 6,074,408 A | 6/2000 | Freeman | |
| 6,086,530 A | 7/2000 | Mack | |
| 6,090,108 A | 7/2000 | McBrayer et al. | |
| 6,096,046 A | 8/2000 | Weiss | |
| 6,110,154 A | 8/2000 | Shimomura et al. | |
| 6,110,183 A | 8/2000 | Cope | |
| 6,113,593 A | 9/2000 | Tu et al. | |
| 6,117,144 A * | 9/2000 | Nobles et al. ................ 606/144 | |
| 6,117,158 A | 9/2000 | Measamer et al. | |
| 6,139,555 A | 10/2000 | Hart et al. | |
| 6,146,391 A | 11/2000 | Cigaina | |
| 6,149,653 A | 11/2000 | Deslauriers | |
| 6,149,662 A | 11/2000 | Pugliesi et al. | |
| 6,159,200 A | 12/2000 | Verdura et al. | |
| 6,165,184 A | 12/2000 | Verdura et al. | |
| 6,168,570 B1 | 1/2001 | Ferrera | |
| 6,168,605 B1 | 1/2001 | Measamer et al. | |
| 6,170,130 B1 | 1/2001 | Hamilton et al. | |
| 6,179,776 B1 | 1/2001 | Adams et al. | |
| 6,179,837 B1 | 1/2001 | Hooven | |
| 6,183,420 B1 | 2/2001 | Douk et al. | |
| 6,190,353 B1 | 2/2001 | Makower et al. | |
| 6,190,384 B1 | 2/2001 | Ouchi | |
| 6,190,399 B1 | 2/2001 | Palmer et al. | |
| 6,203,533 B1 | 3/2001 | Ouchi | |
| 6,206,872 B1 | 3/2001 | Lafond et al. | |
| 6,206,877 B1 | 3/2001 | Kese et al. | |
| 6,214,007 B1 | 4/2001 | Anderson | |
| 6,228,096 B1 | 5/2001 | Marchand | |
| 6,245,079 B1 * | 6/2001 | Nobles et al. ................ 606/144 | |
| 6,246,914 B1 | 6/2001 | de la Rama et al. | |
| 6,258,064 B1 | 7/2001 | Smith et al. | |
| 6,261,242 B1 | 7/2001 | Roberts et al. | |
| 6,264,664 B1 | 7/2001 | Avellanet | |
| 6,270,497 B1 | 8/2001 | Sekino et al. | |
| 6,270,505 B1 | 8/2001 | Yoshida et al. | |
| 6,277,136 B1 | 8/2001 | Bonutti | |
| 6,283,963 B1 | 9/2001 | Regula | |
| 6,293,909 B1 | 9/2001 | Chu et al. | |
| 6,293,952 B1 | 9/2001 | Brosens et al. | |
| 6,296,630 B1 | 10/2001 | Altman et al. | |
| 6,322,578 B1 | 11/2001 | Houle et al. | |
| 6,326,177 B1 | 12/2001 | Schoenbach et al. | |
| 6,328,730 B1 | 12/2001 | Harkrider, Jr. | |
| 6,350,267 B1 | 2/2002 | Stefanchik | |
| 6,350,278 B1 | 2/2002 | Lenker et al. | |
| 6,352,503 B1 | 3/2002 | Matsui et al. | |
| 6,352,543 B1 | 3/2002 | Cole | |
| 6,355,035 B1 | 3/2002 | Manushakian | |
| 6,371,956 B1 | 4/2002 | Wilson et al. | |
| 6,379,366 B1 | 4/2002 | Fleischman et al. | |
| 6,383,195 B1 | 5/2002 | Richard | |
| 6,383,197 B1 | 5/2002 | Conlon et al. | |
| 6,391,029 B1 | 5/2002 | Hooven et al. | |
| 6,402,735 B1 | 6/2002 | Langevin | |
| 6,406,440 B1 | 6/2002 | Stefanchik | |
| 6,409,733 B1 | 6/2002 | Conlon et al. | |
| 6,431,500 B1 | 8/2002 | Jacobs et al. | |
| 6,447,511 B1 | 9/2002 | Slater | |
| 6,447,523 B1 | 9/2002 | Middleman et al. | |
| 6,454,783 B1 | 9/2002 | Piskun | |
| 6,454,785 B2 | 9/2002 | De Hoyos Garza | |
| 6,464,701 B1 | 10/2002 | Hooven et al. | |
| 6,475,104 B1 | 11/2002 | Lutz et al. | |
| 6,485,411 B1 | 11/2002 | Konstorum et al. | |
| 6,489,745 B1 | 12/2002 | Koreis | |
| 6,491,626 B1 | 12/2002 | Stone et al. | |
| 6,491,691 B1 | 12/2002 | Morley et al. | |
| 6,493,590 B1 | 12/2002 | Wessman et al. | |
| 6,494,893 B2 | 12/2002 | Dubrul et al. | |
| 6,503,192 B1 | 1/2003 | Ouchi | |
| 6,506,190 B1 | 1/2003 | Walshe | |
| 6,508,827 B1 | 1/2003 | Manhes | |
| 6,543,456 B1 | 4/2003 | Freeman | |
| 6,551,270 B1 | 4/2003 | Bimbo et al. | |
| 6,554,829 B2 | 4/2003 | Schulze et al. | |
| 6,558,384 B2 | 5/2003 | Mayenberger | |
| 6,562,035 B1 | 5/2003 | Levin | |
| 6,562,052 B2 * | 5/2003 | Nobles et al. ................ 606/144 | |
| 6,569,159 B1 | 5/2003 | Edwards et al. | |
| 6,572,629 B2 | 6/2003 | Kalloo et al. | |
| 6,572,635 B1 | 6/2003 | Bonutti | |
| 6,575,988 B2 | 6/2003 | Rousseau | |
| 6,579,311 B1 | 6/2003 | Makower | |
| 6,585,642 B2 | 7/2003 | Christopher | |
| 6,585,717 B1 | 7/2003 | Wittenberger et al. | |
| 6,592,559 B1 | 7/2003 | Pakter et al. | |
| 6,592,603 B2 | 7/2003 | Lasner | |
| 6,602,262 B2 | 8/2003 | Griego et al. | |
| 6,605,105 B1 | 8/2003 | Cuschieri et al. | |
| 6,610,072 B1 | 8/2003 | Christy et al. | |
| 6,610,074 B2 | 8/2003 | Santilli | |
| 6,626,919 B1 | 9/2003 | Swanstrom | |
| 6,632,229 B1 | 10/2003 | Yamanouchi | |
| 6,638,286 B1 * | 10/2003 | Burbank et al. ................ 606/157 | |
| 6,652,521 B2 | 11/2003 | Schulze | |
| 6,652,551 B1 | 11/2003 | Heiss | |
| 6,656,194 B1 | 12/2003 | Gannoe et al. | |
| 6,663,641 B1 | 12/2003 | Kovac et al. | |
| 6,666,854 B1 | 12/2003 | Lange | |
| 6,672,338 B1 | 1/2004 | Esashi et al. | |
| 6,673,087 B1 | 1/2004 | Chang et al. | |
| 6,685,628 B2 | 2/2004 | Vu | |
| 6,685,724 B1 | 2/2004 | Haluck | |
| 6,692,445 B2 | 2/2004 | Roberts et al. | |
| 6,692,462 B2 | 2/2004 | Mackenzie et al. | |
| 6,699,180 B2 | 3/2004 | Kobayashi | |
| 6,699,256 B1 | 3/2004 | Logan et al. | |
| 6,699,263 B2 | 3/2004 | Cope | |
| 6,708,066 B2 | 3/2004 | Herbst et al. | |
| 6,716,226 B2 | 4/2004 | Sixto, Jr. et al. | |
| 6,740,030 B2 | 5/2004 | Martone et al. | |
| 6,743,240 B2 | 6/2004 | Smith et al. | |
| 6,749,560 B1 | 6/2004 | Konstorum et al. | |
| 6,749,609 B1 | 6/2004 | Lunsford et al. | |
| 6,752,768 B2 | 6/2004 | Burdorff et al. | |
| 6,752,811 B2 | 6/2004 | Chu et al. | |
| 6,752,822 B2 | 6/2004 | Jespersen | |
| 6,761,685 B2 | 7/2004 | Adams et al. | |
| 6,761,718 B2 | 7/2004 | Madsen | |
| 6,773,434 B2 | 8/2004 | Ciarrocca | |
| 6,780,151 B2 | 8/2004 | Grabover et al. | |
| 6,780,352 B2 | 8/2004 | Jacobson | |
| 6,783,491 B2 | 8/2004 | Saadat et al. | |
| 6,786,864 B2 | 9/2004 | Matsuura et al. | |
| 6,790,173 B2 | 9/2004 | Saadat et al. | |
| 6,795,728 B2 | 9/2004 | Chornenky et al. | |
| 6,800,056 B2 | 10/2004 | Tartaglia et al. | |
| 6,808,491 B2 | 10/2004 | Kortenbach et al. | |
| 6,824,548 B2 | 11/2004 | Smith et al. | |
| 6,837,847 B2 | 1/2005 | Ewers et al. | |
| 6,843,794 B2 | 1/2005 | Sixto, Jr. et al. | |
| 6,861,250 B1 | 3/2005 | Cole et al. | |
| 6,866,627 B2 | 3/2005 | Nozue | |
| 6,878,106 B1 | 4/2005 | Herrmann | |
| 6,878,110 B2 | 4/2005 | Yang et al. | |
| 6,884,213 B2 | 4/2005 | Raz et al. | |
| 6,887,255 B2 | 5/2005 | Shimm | |
| 6,896,683 B1 | 5/2005 | Gadberry et al. | |

| | | |
|---|---|---|
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,195,612 B2 | 3/2007 | Van Sloten et al. |
| 7,195,631 B2 | 3/2007 | Dumbauld |
| 7,208,005 B2 | 4/2007 | Frecker et al. |
| 7,211,092 B2 | 5/2007 | Hughett |
| 7,223,272 B2 | 5/2007 | Francere et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,222 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,534,228 B2 | 5/2009 | Williams |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,713,270 B2 | 5/2010 | Suzuki |
| 7,736,374 B2 | 6/2010 | Vaughan et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,794,475 B2 | 9/2010 | Hess et al. |
| 7,837,615 B2 | 11/2010 | Le et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,896,887 B2 | 3/2011 | Rimbaugh et al. |
| 7,918,869 B2 | 4/2011 | Saadat et al. |
| 7,931,624 B2 | 4/2011 | Smith et al. |
| 7,947,000 B2 | 5/2011 | Vargas et al. |
| 7,955,298 B2 | 6/2011 | Carroll et al. |
| 7,963,975 B2 | 6/2011 | Criscuolo |
| 2001/0049497 A1 | 12/2001 | Kalloo et al. |

| Publication No. | Date | Inventor |
|---|---|---|
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0114732 A1 | 6/2003 | Webler et al. |
| 2003/0120257 A1 | 6/2003 | Houston et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |

| | | | | | |
|---|---|---|---|---|---|
| 2006/0111704 A1 | 5/2006 | Brenneman et al. | 2007/0112384 A1 | 5/2007 | Conlon et al. |
| 2006/0129166 A1 | 6/2006 | Lavelle | 2007/0112385 A1 | 5/2007 | Conlon |
| 2006/0135962 A1 | 6/2006 | Kick et al. | 2007/0112417 A1 | 5/2007 | Shanley et al. |
| 2006/0135971 A1 | 6/2006 | Swanstrom et al. | 2007/0112425 A1 | 5/2007 | Schaller et al. |
| 2006/0135984 A1 | 6/2006 | Kramer et al. | 2007/0118115 A1 | 5/2007 | Artale et al. |
| 2006/0142644 A1 | 6/2006 | Mulac et al. | 2007/0122425 A1 | 5/2007 | Schaller et al. |
| 2006/0142652 A1 | 6/2006 | Keenan | 2007/0123840 A1 | 5/2007 | Cox |
| 2006/0142790 A1 | 6/2006 | Gertner | 2007/0129605 A1 | 6/2007 | Schaaf |
| 2006/0142798 A1 | 6/2006 | Holman et al. | 2007/0129719 A1 | 6/2007 | Kendale et al. |
| 2006/0149132 A1 | 7/2006 | Iddan | 2007/0135709 A1 | 6/2007 | Rioux et al. |
| 2006/0149135 A1 | 7/2006 | Paz | 2007/0142706 A1 | 6/2007 | Matsui et al. |
| 2006/0161190 A1 | 7/2006 | Gadberry et al. | 2007/0156127 A1 | 7/2007 | Rioux et al. |
| 2006/0167416 A1 | 7/2006 | Mathis et al. | 2007/0161855 A1 | 7/2007 | Mikkaichi et al. |
| 2006/0167482 A1 | 7/2006 | Swain et al. | 2007/0173691 A1 | 7/2007 | Yokoi et al. |
| 2006/0178560 A1 | 8/2006 | Saadat et al. | 2007/0173869 A1 | 7/2007 | Gannoe et al. |
| 2006/0183975 A1 | 8/2006 | Saadat et al. | 2007/0173870 A2 | 7/2007 | Zacharias |
| 2006/0184161 A1 | 8/2006 | Maahs et al. | 2007/0173872 A1 | 7/2007 | Neuenfeldt |
| 2006/0189844 A1 | 8/2006 | Tien | 2007/0179525 A1 | 8/2007 | Frecker et al. |
| 2006/0189845 A1 | 8/2006 | Maahs et al. | 2007/0179530 A1 | 8/2007 | Tieu et al. |
| 2006/0190027 A1 | 8/2006 | Downey | 2007/0197865 A1 | 8/2007 | Miyake et al. |
| 2006/0195084 A1 | 8/2006 | Slater | 2007/0203487 A1 | 8/2007 | Sugita |
| 2006/0200005 A1 | 9/2006 | Bjork et al. | 2007/0208364 A1 | 9/2007 | Smith et al. |
| 2006/0200169 A1 | 9/2006 | Sniffin | 2007/0213754 A1 | 9/2007 | Mikkaichi et al. |
| 2006/0200170 A1 | 9/2006 | Aranyi | 2007/0225554 A1 | 9/2007 | Maseda et al. |
| 2006/0200199 A1 | 9/2006 | Bonutti et al. | 2007/0233040 A1 | 10/2007 | Macnamara et al. |
| 2006/0217665 A1 | 9/2006 | Prosek | 2007/0244358 A1 | 10/2007 | Lee |
| 2006/0217697 A1 | 9/2006 | Lau et al. | 2007/0250057 A1 | 10/2007 | Nobis et al. |
| 2006/0217742 A1 | 9/2006 | Messerly et al. | 2007/0255096 A1 | 11/2007 | Stefanchik et al. |
| 2006/0217743 A1 | 9/2006 | Messerly et al. | 2007/0255100 A1 | 11/2007 | Barlow et al. |
| 2006/0229639 A1 | 10/2006 | Whitfield | 2007/0255273 A1 | 11/2007 | Fernandez et al. |
| 2006/0229640 A1 | 10/2006 | Whitfield | 2007/0255303 A1 | 11/2007 | Bakos et al. |
| 2006/0237022 A1 | 10/2006 | Chen et al. | 2007/0255306 A1 | 11/2007 | Conlon et al. |
| 2006/0237023 A1 | 10/2006 | Cox et al. | 2007/0260112 A1 | 11/2007 | Rahmani |
| 2006/0241570 A1 | 10/2006 | Wilk | 2007/0260117 A1 | 11/2007 | Zwolinski et al. |
| 2006/0247673 A1 | 11/2006 | Voegele et al. | 2007/0260121 A1 | 11/2007 | Bakos et al. |
| 2006/0253004 A1 | 11/2006 | Frisch et al. | 2007/0260273 A1 | 11/2007 | Cropper et al. |
| 2006/0253039 A1 | 11/2006 | McKenna et al. | 2007/0270629 A1 | 11/2007 | Charles |
| 2006/0258907 A1 | 11/2006 | Stefanchik et al. | 2007/0270889 A1 | 11/2007 | Conlon et al. |
| 2006/0258908 A1 | 11/2006 | Stefanchik et al. | 2007/0270895 A1 | 11/2007 | Nobis et al. |
| 2006/0258910 A1 | 11/2006 | Stefanchik et al. | 2007/0270907 A1 | 11/2007 | Stokes et al. |
| 2006/0258954 A1 | 11/2006 | Timberlake et al. | 2007/0282371 A1 | 12/2007 | Lee et al. |
| 2006/0258955 A1 | 11/2006 | Hoffman et al. | 2007/0299387 A1 | 12/2007 | Williams et al. |
| 2006/0259010 A1 | 11/2006 | Stefanchik et al. | 2008/0004650 A1 | 1/2008 | George |
| 2006/0264752 A1 | 11/2006 | Rubinsky et al. | 2008/0015409 A1 | 1/2008 | Barlow et al. |
| 2006/0264904 A1 | 11/2006 | Kerby et al. | 2008/0015552 A1 | 1/2008 | Doyle et al. |
| 2006/0264930 A1 | 11/2006 | Nishimura | 2008/0027387 A1 | 1/2008 | Grabinsky |
| 2006/0270902 A1 | 11/2006 | Igarashi et al. | 2008/0033451 A1 | 2/2008 | Rieber et al. |
| 2006/0271102 A1 | 11/2006 | Bosshard et al. | 2008/0051629 A1 | 2/2008 | Sugiyama et al. |
| 2006/0276835 A1 | 12/2006 | Uchida | 2008/0051735 A1 | 2/2008 | Measamer et al. |
| 2006/0281970 A1 | 12/2006 | Stokes et al. | 2008/0058586 A1 | 3/2008 | Karpiel |
| 2006/0282106 A1 | 12/2006 | Cole et al. | 2008/0065169 A1 | 3/2008 | Colliou et al. |
| 2006/0285732 A1 | 12/2006 | Horn et al. | 2008/0086172 A1 | 4/2008 | Martin et al. |
| 2006/0287644 A1 | 12/2006 | Inganas et al. | 2008/0097472 A1 | 4/2008 | Agmon et al. |
| 2006/0287666 A1 | 12/2006 | Saadat et al. | 2008/0097483 A1 | 4/2008 | Ortiz et al. |
| 2006/0293626 A1 | 12/2006 | Byrum et al. | 2008/0103527 A1 | 5/2008 | Martin et al. |
| 2007/0002135 A1 | 1/2007 | Glukhovsky | 2008/0114384 A1 | 5/2008 | Chang et al. |
| 2007/0005019 A1 | 1/2007 | Okishige | 2008/0119870 A1 | 5/2008 | Williams |
| 2007/0015965 A1 | 1/2007 | Cox et al. | 2008/0125796 A1 | 5/2008 | Graham |
| 2007/0016255 A1 | 1/2007 | Nakao | 2008/0132892 A1 | 6/2008 | Lunsford et al. |
| 2007/0032700 A1 | 2/2007 | Fowler et al. | 2008/0139882 A1 | 6/2008 | Fujimori |
| 2007/0032701 A1 | 2/2007 | Fowler et al. | 2008/0147113 A1 | 6/2008 | Nobis et al. |
| 2007/0043261 A1 | 2/2007 | Watanabe et al. | 2008/0171907 A1 | 7/2008 | Long et al. |
| 2007/0043345 A1 | 2/2007 | Davalos et al. | 2008/0188868 A1 | 8/2008 | Weitzner et al. |
| 2007/0049800 A1 | 3/2007 | Boulais | 2008/0200755 A1 | 8/2008 | Bakos |
| 2007/0049902 A1 | 3/2007 | Griffin et al. | 2008/0200762 A1 | 8/2008 | Stokes et al. |
| 2007/0051375 A1 | 3/2007 | Milliman | 2008/0200911 A1 | 8/2008 | Long |
| 2007/0060880 A1 | 3/2007 | Gregorich et al. | 2008/0200912 A1 | 8/2008 | Long |
| 2007/0067017 A1 | 3/2007 | Trapp | 2008/0200933 A1 | 8/2008 | Bakos et al. |
| 2007/0073102 A1 | 3/2007 | Matsuno et al. | 2008/0200934 A1 | 8/2008 | Fox |
| 2007/0073269 A1 | 3/2007 | Becker | 2008/0208213 A1 | 8/2008 | Benjamin et al. |
| 2007/0079924 A1 | 4/2007 | Saadat et al. | 2008/0221587 A1 | 9/2008 | Schwartz |
| 2007/0088370 A1 | 4/2007 | Kahle et al. | 2008/0221619 A1 | 9/2008 | Spivey et al. |
| 2007/0100375 A1 | 5/2007 | Mikkaichi et al. | 2008/0228213 A1 | 9/2008 | Blakeney et al. |
| 2007/0100376 A1 | 5/2007 | Mikkaichi et al. | 2008/0230972 A1 | 9/2008 | Ganley |
| 2007/0106118 A1 | 5/2007 | Moriyama | 2008/0234696 A1 | 9/2008 | Taylor et al. |
| 2007/0112251 A1 | 5/2007 | Nakhuda | 2008/0243106 A1 | 10/2008 | Coe et al. |
| 2007/0112331 A1 | 5/2007 | Weber et al. | 2008/0243148 A1 | 10/2008 | Mikkaichi et al. |
| 2007/0112342 A1 | 5/2007 | Pearson et al. | 2008/0243176 A1 | 10/2008 | Weitzner et al. |
| 2007/0112383 A1 | 5/2007 | Conlon et al. | 2008/0262540 A1 | 10/2008 | Bangera et al. |

| | | |
|---|---|---|
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0198231 A1 | 8/2009 | Esser et al. |
| 2009/0227828 A1 | 9/2009 | Swain et al. |
| 2009/0248055 A1 | 10/2009 | Spivey et al. |
| 2009/0281559 A1 | 11/2009 | Swain et al. |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Filho |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |

FOREIGN PATENT DOCUMENTS

| | | |
|---|---|---|
| DE | 3008120 A1 | 9/1980 |
| DE | 4323585 A1 | 1/1995 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 1769749 B1 | 11/2009 |

| | | | |
|---|---|---|---|
| FR | 2731610 A1 | 9/1996 |
| GB | 330629 A | 6/1930 |
| GB | 2403909 A | 1/2005 |
| GB | 2421190 A | 6/2006 |
| GB | 2443261 A | 4/2008 |
| JP | 56-46674 | 4/1981 |
| JP | 8-29699 A | 2/1996 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/09919 A1 | 3/1999 |
| WO | WO 99/17661 A1 | 4/1999 |
| WO | WO 99/30622 A2 | 6/1999 |
| WO | WO 01/10319 A1 | 2/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059012 A2 | 7/2003 |
| WO | WO 03/078721 A2 | 9/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/101075 A2 | 8/2008 |
| WO | WO 2008/102154 A2 | 8/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2010/088481 A1 | 8/2010 |

OTHER PUBLICATIONS

J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual. Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
Partial International Search Report for PCT/US2008/061359, Oct. 21, 2008 (2 pages).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Interv Radio!, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).
U.S. Appl. No. 11/744,271, filed May 4, 2007.
U.S. Appl. No. 11/744,279, filed May 4, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489 filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 11/756,914, filed Jun. 1, 2007.
U.S. Appl. No. 12/060,601, filed Apr. 1, 2008.
U.S. Appl. No. 11/952,475, filed Dec. 7, 2007.
U.S. Appl. No. 12/277,975, filed Nov. 25, 2008.
U.S. Appl. No. 12/277,957, filed Nov. 25, 2008.
D. Wilhelm et al., "An Innovative, Safe and Sterile Sigmoid Access (ISSA) for Notes," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential Of Pure Notes Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using A Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using A Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://vvww.medgadget.com/archives/2010/01/octo_port_modular_laparo...; accessed Jan. 5, 2010 (4 pages).

Hakko Retractors, obtained Aug. 25, 2009 (5 pages).

Zadno et al., "Linear Superelasticity in Cold-Worked NI-TI," Engineering Aspects of Shape Memory Alloys, pp. 414-419.

U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.

International Preliminary Report on Patentability for PCT/US2008/061359, Nov. 5, 2009 (6 pages).

Zadno et al., "Linear Superelasticity in Cold-Worked NI-TI," Engineering Aspects of Shape Memory Alloys, pp. 414-419 (1990).

* cited by examiner

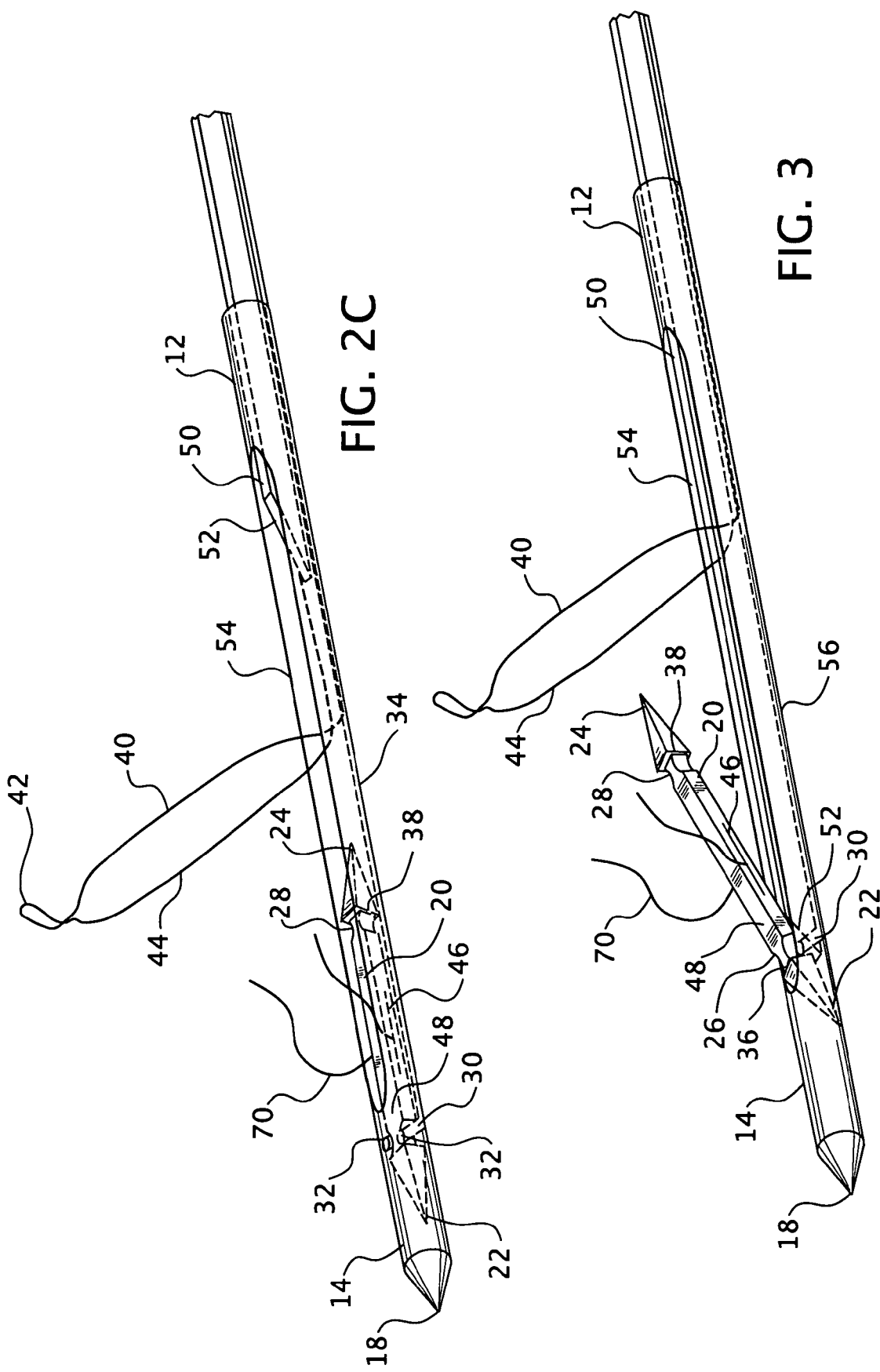

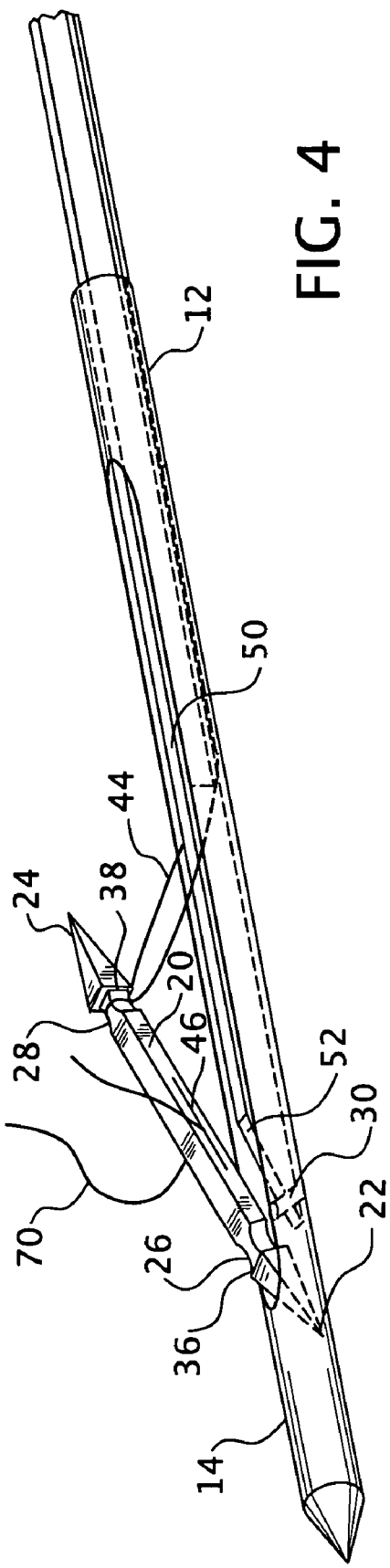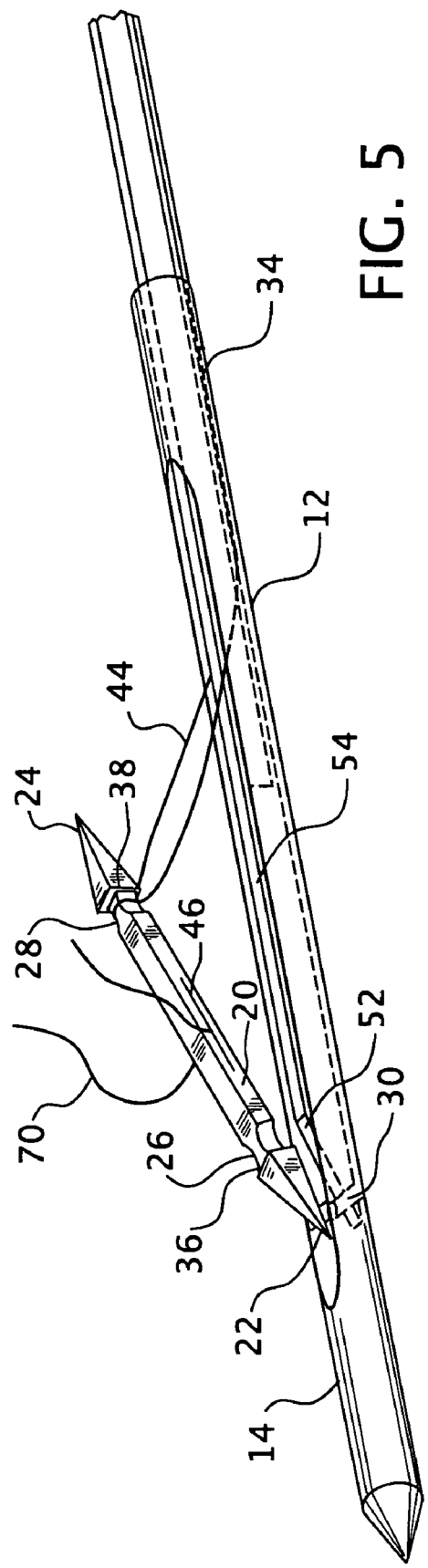

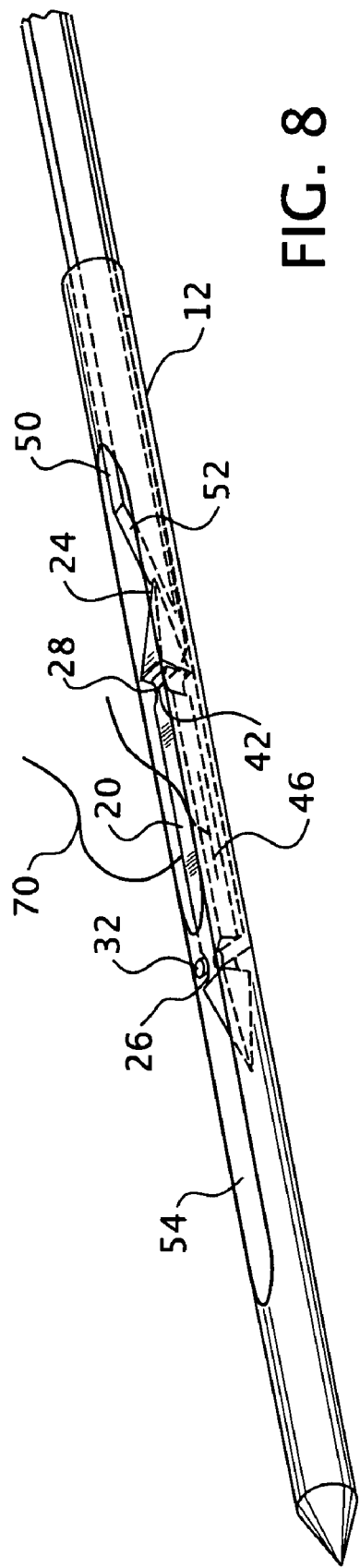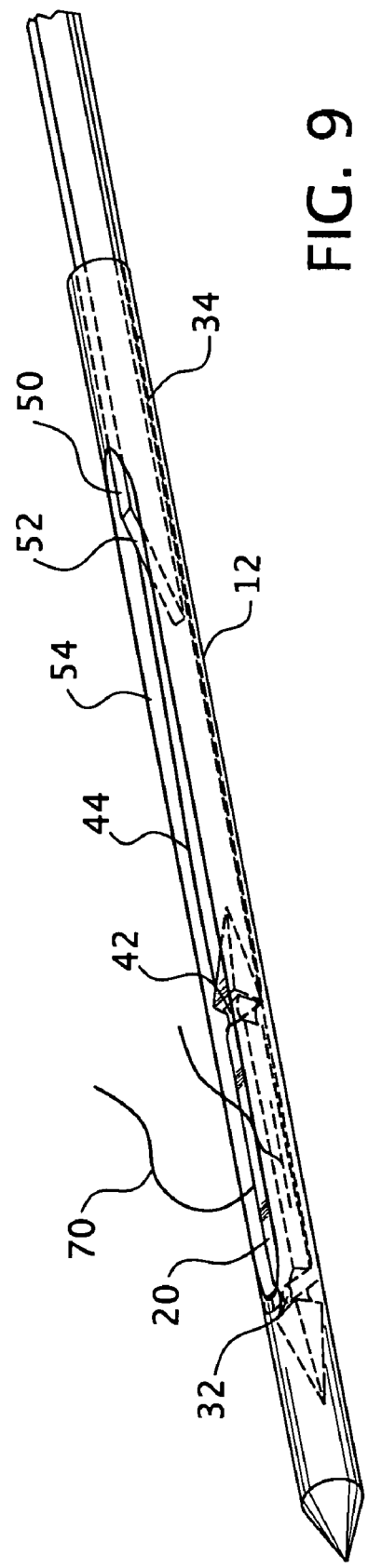

SURGICAL SUTURING APPARATUS

FIELD OF THE INVENTION

The present invention relates to tools for surgical suturing, and more particularly, to a tool for endoscopic surgical suturing, including natural orifice transenteric surgery.

BACKGROUND

Sutures are used to approximate, or bring together, tissue separated, for example, by some trauma, or wound or during a surgical procedure to close an incision or an organ perforation. Suturing instruments generally include a needle and a trailing length of suture material. In endoscopic procedures, the instruments placed through an instrument channel may include needles and sutures for stitching such a wound, incision or perforation within the patient's body cavity. An exemplary suturing device is shown in U.S. Pat. No. 7,131,978.

Physicians have often used endoscopes to examine, to biopsy, and to ablate the tissue of patients within lumens such as the esophagus and the bowel or other body cavity and internal patient sites. An endoscope generally includes either a rigid or flexible tube containing one or more optical fiber systems and, for operative uses (human or veterinary), one or more channels for passage of medical instruments. The optical system includes a light delivery system to illuminate the organ or site under inspection and a camera system to transmit the image of the site of interest to the viewer. The light source is normally outside the body and the light is typically directed via optical fiber bundles to the area of interest. A physician performing a therapeutic procedure with the use of an endoscope places a long, flexible instrument through the endoscope's instrument channel and then positions the instrument near the site within the body cavity, lumen or other internal site of interest where a therapeutic procedure is to be performed.

A physician performing a therapeutic procedure with the use of an endoscope places a long, flexible instrument through the endoscope's instrument channel and then positions the instrument near the site within the body lumen where a procedure is to be performed. The instrument channels and optical fiber bundles open into the body at the distal end of the endoscope and are generally parallel to the axis of the flexible endoscope. Physicians place flexible instruments through the instrument channels while visualizing and illuminating an internal site using the optical fiber bundles.

More recently, a surgical technique known as natural orifice transenteric surgery (NOTES) is attracting interest. NOTES, which enables "scarless" abdominal operations, may be performed with an endoscope that is passed through a natural orifice (mouth, nose, anus, etc.), then through an internal incision in the stomach or colon, for example, thus avoiding any external incisions or scars. The NOTES technique has been used for diagnostic and therapeutic procedures in animal models, including transgastric (through the stomach) organ removal. Transcolonic approaches are also advocated for access to upper abdominal structures that may be more difficult to work with using a transgastric approach.

SUMMARY OF THE INVENTION

An improved surgical suturing apparatus is provided. The suturing apparatus has a needle, a channel, and members for moving the needle. The channel has a longitudinal axis, a distal end and a proximal end, and defines a housing at its distal end having an opening therein. The needle is releasably disposed within the housing and has a first end and a first puncturing point at a second end thereof. The needle includes a structure, such as an eye, slot, hook, sleeve or similar structure, for attachment to a length of suture material. The needle preferably has a first engagement surface adjacent the first end and a second engagement surface adjacent the first puncturing point.

The suturing apparatus also includes a needle positioning assembly having members movable relative to the channel for effecting a desired number of release and retrieval cycles for releasing the needle from the housing and guiding the return of the needle to the housing. An actuation assembly for controlling the members of the needle positioning assembly is also provided. When a length of suture material is attached to the needle, the puncture of tissue with the first puncturing point and movement of the needle through tissue in a first direction threads the suture material through the tissue to provide a stitch.

At least one suture tag may be provided. Each suture tag has at least one passage therethrough for attachment to the suture material. The suture tags may be configured for attachment at one or both of the ends of the length of suture for securing the suture to the tissue at the start of and/or at the completion of suturing. The needle may be left in place following suturing to function as a suture tag to secure the suture against slipping. An alternative suture tag design includes inner and outer tapered cylinders. The inner cylinder may be co-axial relative to and axially movable within the outer cylinder in a telescoping manner. At least one passage is provided in each of the inner and outer cylinders. In one embodiment, the inner cylinder has two passages for passage of the length of suture material. The inner cylinder may be wedged into the outer cylinder to lock the suture tag and the suture in place at the sutured site.

In one embodiment, the needle positioning assembly may include an engagement member, a ramp member and a snare member. The engagement member is configured for releasably engaging the needle to effect axial movement of the needle within the channel. The ramp member is movable axially within the channel and is configured for operative contact with the needle for effecting movement of the needle to a first stage of progression adjacent the opening of the housing and to a second stage of progression wherein at least the first puncturing point is out of the housing. The snare member is movable and has a portion configured for engagement with the needle for guiding the needle when the needle is out of the housing. The portion of the snare member may comprise a noose for engagement with the second engagement surface of the needle, an expandable loop proximal to the noose and biased away from the longitudinal axis of the channel, and an elongate section proximal to the loop and operatively connected to the actuation assembly. In one embodiment, movement of the elongate section in the distal direction positions the noose and loop adjacent the opening of the housing to enable the release of the loop and noose from the channel, and movement of the elongate section in the proximal direction when the noose and loop are out of the channel effects the return of the loop and the noose to the channel.

The ramp member of the needle positioning assembly may include a rail operatively connected to the actuation assembly at a proximal end of the rail and a slope at a distal end of the rail for contact with the needle. In this embodiment, the slope, when moved into the second stage of progression, urges the needle from the housing at an angle to position the first puncturing point at a desired location for puncturing tissue.

The engagement member of the needle positioning assembly may include an elongate portion operatively connected to the actuation assembly and a pair of tines for engaging the needle at the first engagement surface.

In one embodiment, the actuation assembly includes a body portion, a handle and a plurality of rods operatively connected to the members of the positioning assembly for controlling movement of the needle. The plurality of rods in this embodiment may include a first push rod housed in the body portion and operatively connected to the handle and the engagement member for driving axial movement of the engagement member, a second push rod housed in the body portion and operatively connected to the handle and the ramp member for driving axial movement of the ramp member to the first stage of progression and for driving movement of the ramp member in the second stage of progression, a lock mechanism for locking the second push rod against movement of the ramp member to the second stage of progression, a release mechanism for selectively unlocking the second push rod to trigger movement of the ramp member to the second stage of progression, and a third push rod housed in the body portion and operatively connected to the handle and the snare member for driving axial movement of the snare member to a position for release of the portion of the snare from the channel and for return of the portion to the channel.

In one embodiment of the suturing apparatus, movement of the third push rod in a distal direction positions the portion of the snare member within the opening in the housing to effect the release of the portion of the snare member for engagement with the needle, and movement of the third push rod in a proximal direction when the portion engages the needle effects (i) the proximal travel of the needle when the needle is out of the housing to pull the needle through tissue in the proximal direction and (ii) the return of the portion of the snare member and the needle to the channel. The actuation assembly may further include a trigger for moving the snare portion distally to the opening in the housing.

The lock mechanism may include a pin or a similar structure extending outwardly from the second push rod, and a locking plate having a notch therein for stopping the pin against movement in a distal direction beyond the notch. The release mechanism in this embodiment may comprise a lever for lifting the locking plate to release the pin from the notch.

The channel may be configured at the distal end thereof to enable the puncture of tissue in a first direction. Alternatively, the channel may be open at the distal end thereof to expose a second puncturing point at the first end of the needle to effect a puncture of tissue in a first direction when the channel is moved in the first direction. When a length of suture material is attached to the eye of the needle, the puncture of tissue with the second puncturing point and movement of the needle through the tissue in the first direction threads the suture material through the tissue. The puncture of tissue with the first puncturing point and movement of the needle through the tissue in a second direction threads the suture material through the tissue in the second direction to define a first stitch through the tissue. Multiple stitches may be made in this manner.

Methods of suturing with the suturing apparatus and a method for sterilizing the suturing apparatus are also provided.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2C is a partial view of the embodiment of the channel member of FIG. 2A showing the embodiment of the needle of FIG. 2B in the needle housing;

FIG. 3 is a partial view of an embodiment of the channel member showing the ramp pushing the needle of FIG. 2C out of the needle housing.

FIG. 4 is a partial view of the channel member showing the snare lowered onto the proximal neck of the needle.

FIG. 5 is a partial view of the channel member showing the snare pulling the needle out of the needle housing.

FIG. 8 is a partial view of the channel member showing the needle returned to the needle housing.

FIG. 9 is a partial view of the channel member showing the fork member pushing the needle distally to its starting position within the needle housing.

DETAILED DESCRIPTION

Figure 1:
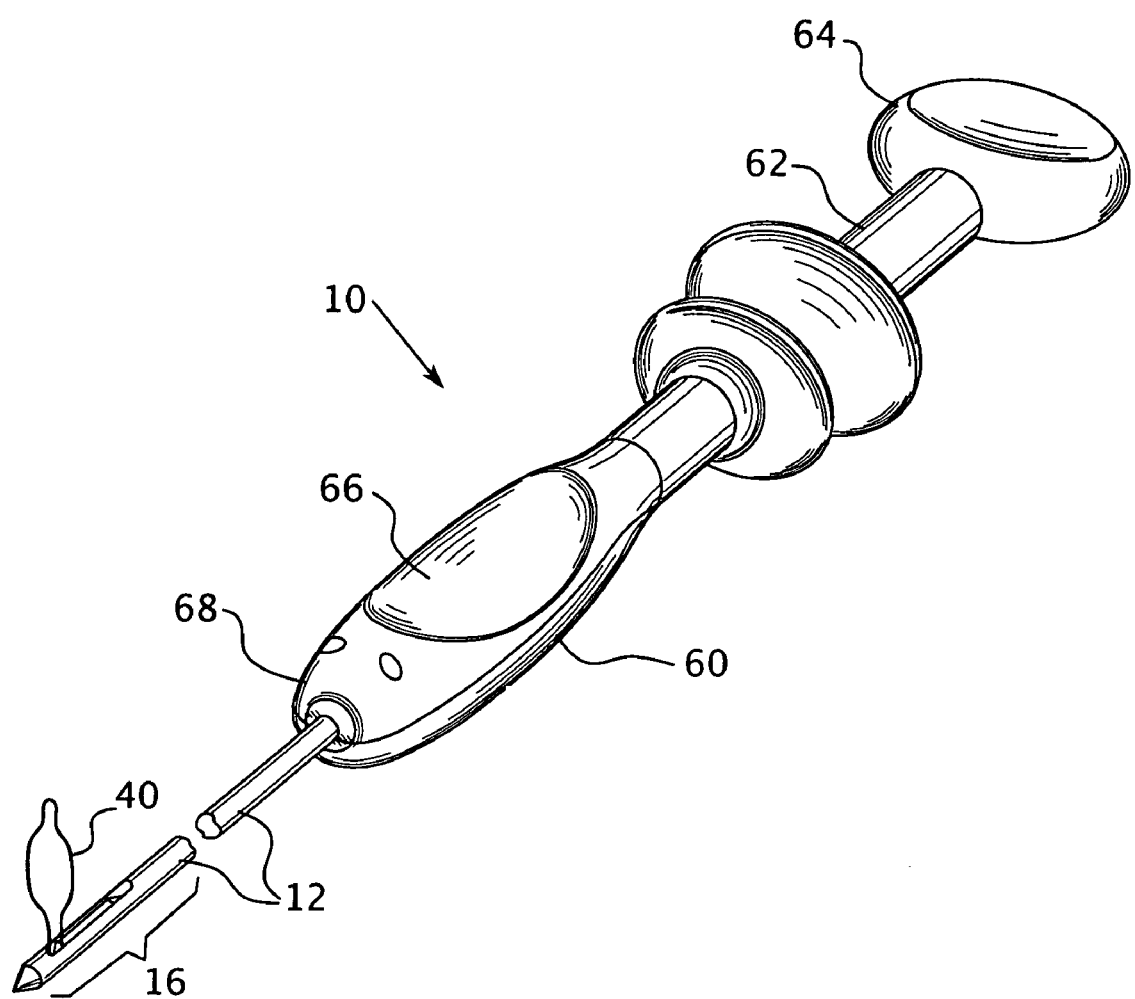
FIG. 1 is a perspective view of an embodiment of the suturing apparatus of the present invention.

Before the present method and embodiments of an instrument are disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims.

Unless defined otherwise, all technical and scientific terms used herein have the same meaning as commonly understood to one of ordinary skill in the art to which this invention belongs. Although any method, instrument and materials similar or equivalent to those described herein may be used in the practice or testing of the invention, particular embodiments of a method, instrument and materials are now described.

It must be noted that, as used in this specification and the appended claims, the singular forms "a," "an," and "the" include plural referents unless the content clearly dictates otherwise.

In describing and claiming the present invention, the following terminology will be used in accordance with the definitions set out below.

As used herein, the term "patient," used herein, refers to any human or animal on which a suturing procedure may be performed.

As used herein, the term "biocompatible" includes any material that is compatible with the living tissues and system(s) of a patient by not being substantially toxic or injurious and not causing immunological rejection. "Biocompatibility" includes the tendency of a material to be biocompatible.

As used herein, the term "bioabsorbable" includes the ability of a material to be dissolved and/or degraded, and absorbed, by the body.

As used herein, the term "integral" or "integrally" means that two or more parts so described are affixed, fastened or joined together so as to move or function together as a substantially unitary part. "Integral" and "integrally" include, but is not limited to, parts that are continuous in the sense that they are formed from the same continuous material, but also includes discontinuous parts that are joined, fastened or affixed together by any means so as to become substantially immovably affixed to, and substantially unitary with, each other.

As used herein, the term "proximal" (or any form thereof), with respect to a component of an instrument, means that portion of the component that is generally nearest the practitioner, physician, or surgeon, or nearest to the end of the instrument handled by the practitioner, physician, or surgeon, when in use; and with respect to a direction of travel of a component of an instrument, means toward the end of the instrument generally nearest the practitioner, physician, or surgeon, or handled by the practitioner, physician, or surgeon, when in use.

As used herein, the term "distal" (or any form thereof), with respect to a component of an instrument, means that portion of the component that is generally farthest from the practitioner, physician, or surgeon, or farthest from the end of the instrument handled by the practitioner, physician, or surgeon, when in use; and with respect to a direction of travel of a component of an instrument, means away from the end of the instrument generally nearest the practitioner, physician, or surgeon, or handled by the practitioner, physician, or surgeon, when in use.

As used herein, the term "longitudinal axis", with respect to an instrument, means the exact or approximate central axis defined by said instrument along its greater dimension, i.e., along its length, from its distal end to its proximal end, and vice versa, and is not intended to be limited to imply a straight line, wherein, for example, an instrument includes a bend angle as described herein, it is intended that "longitudinal axis" as used herein follows such bend angle.

As used herein, the term "axial" or "axial movement" or variants thereof, with respect to an instrument or a component of an instrument, means the movement in the direction of the longitudinal axis of such instrument.

As used herein, the term "operatively connected" with respect to two or more components, means that operation of, movement of, or some action of one component brings about, directly or indirectly, an operation, movement or reaction in the other component or components. Components that are operatively connected may be directly connected, may be indirectly connected to each other with one or more additional components interposed between the two, or may not be connected at all, but within a position such that the operation of, movement of or action of one component effects an operation, movement or reaction in the other component in a causal manner.

As used herein, the term "internal site" of a patient means a lumen, body cavity or other location in a patient's body including, without limitation, sites accessible through natural orifices or through incisions.

The present invention has application in conventional endoscopic and open surgical instrumentation, as well as application in robotic-assisted surgery. The embodiments shown illustrate the use of the invention in connection with an endoscope within an internal site of a patient. The invention is useful in a variety of minimally invasive medical procedures, including without limitation medical procedures performed through laparoscopic incisions for access to body cavities and internal organs of the body. The invention also encompasses apparatus and methods employing endoscopic devices in general, including various forms and variations of endoscopes, including without limitation: laparoscopes, gastroscopes, peritoneoscopes, sigmoidoscopes, fiber optic endoscopes, arthroscopes, amnioscopes, and the like.

The suturing apparatus of the present invention includes a needle, a channel for housing the needle, a needle positioning assembly and an actuation assembly. One embodiment of the suturing apparatus 10 with an embodiment of an actuation assembly is shown generally in FIG. 1. In this embodiment, suturing apparatus 10 includes a body 60, handle knob 64, rod 62, thumb rest 66 and, extending from the distal end 68 thereof, a channel member 12. Channel member 12 may be rigid or flexible, cylindrical or in the form of a C-channel or a like shape suitable for insertion into a patient internal site. Although shown for ease of illustration as relatively short in length, channel member 12 is particularly well suited for use with an endoscope, so may be sized both in length and in cross-section to fit with ease into a working channel of an endoscope (not shown).

In the embodiment of channel member 12 shown in reference to FIGS. 2A and 2C-10, the distal end 14 of channel member 12 has a sharp point or edge 18 for puncturing tissue. In another embodiment, the distal tip of channel 12 can incorporate a veriss needle feature to minimize tissue damage. A veriss needle is used in laparoscopic surgery for blind puncture and consists of a sharpened canula tip about 1 mm in diameter and a distally urged spring loaded blunt tip cylindrical rod that is close fitting inside the canula tip. As the sharp canula point punctures the full thickness of the tissue, the blunt rod is freed (i.e. the rod is no longer compressed against its spring by the tissue to be punctured) to advance past the sharp tip and protect other structures. The distal end of channel member 12 may be dimensioned, in cross-section, to about the size of, or slightly larger than, a standard surgical needle for ease of puncturing and passing through tissue. For example, the distal outer diameter of the end of channel member 12 may be about 0.020 to 0.125 inches (about 0.051 to about 0.317 cm) in diameter (or similar cross-sectional dimension, if not cylindrical in shape).

Figure 2A:
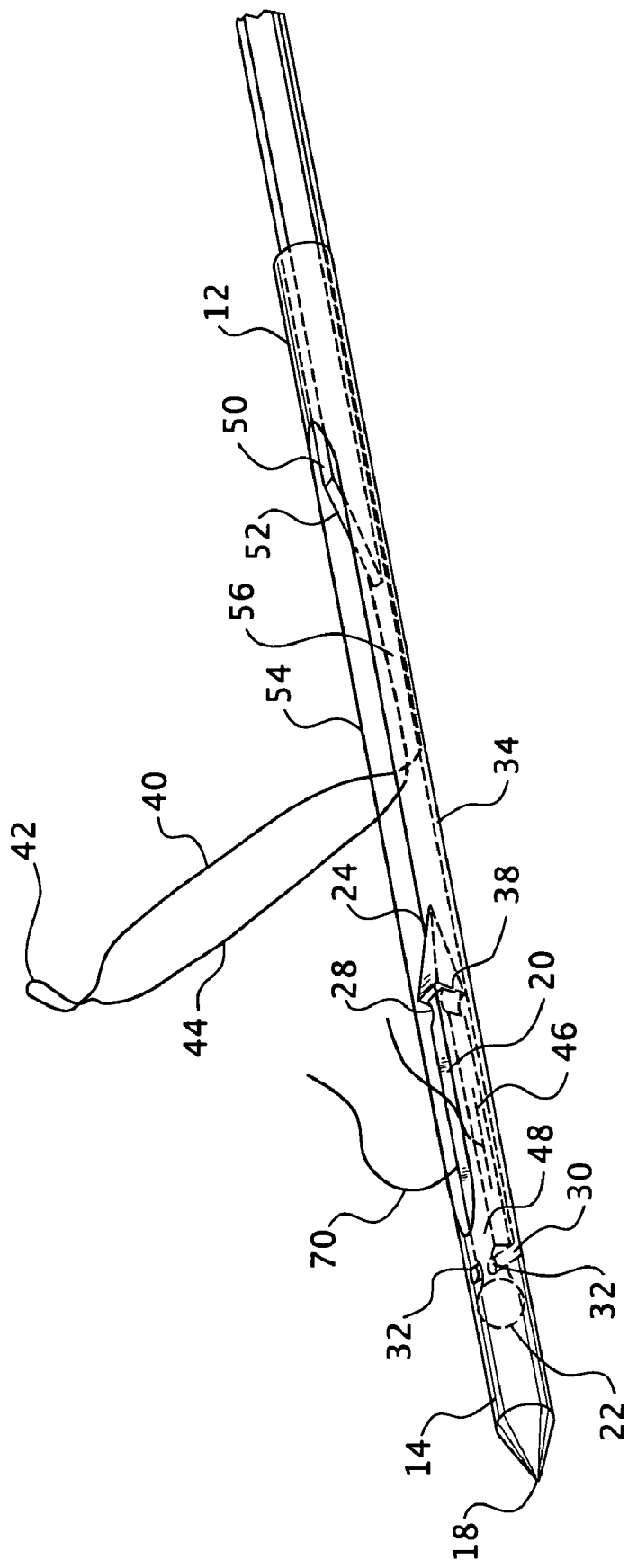
FIG. 2A is a partial view of one embodiment of the channel member showing one embodiment of the needle in the needle housing.
Figure 2B:
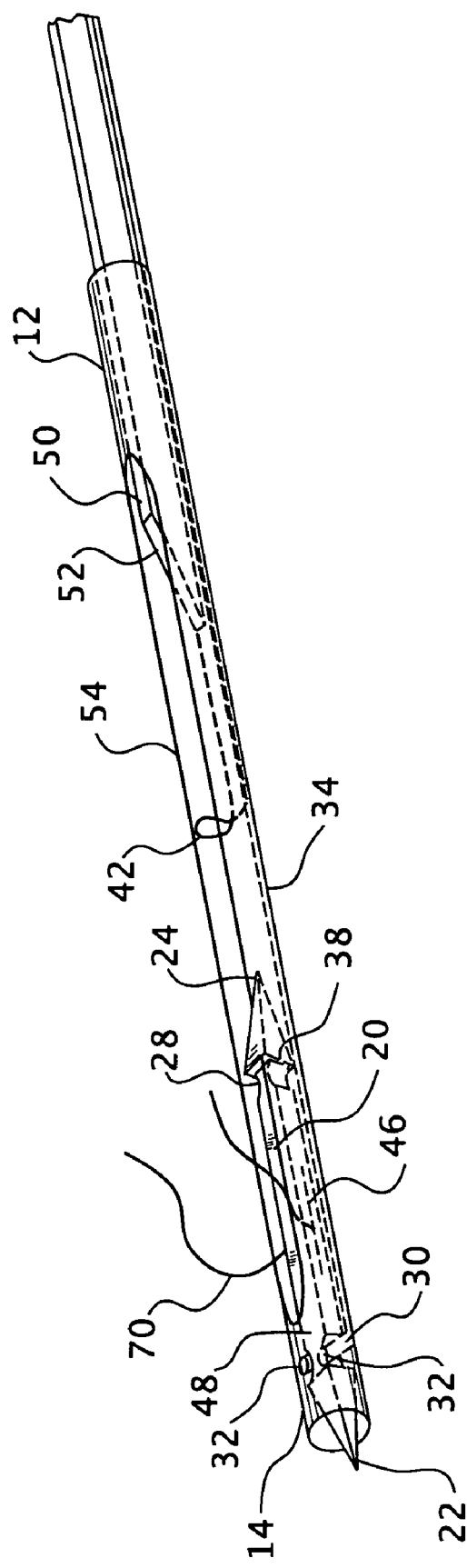
FIG. 2B is a partial view of an alternative embodiment of the channel member showing an alternative embodiment of the needle in the needle housing.

As shown in FIG. 1, distal end 14 also includes a housing area 16 for housing shuttle needle 20. Referring to FIGS. 2A-C, the channel member 12 also houses a fork member 30 for engaging the distal end of needle 20, a ramp member 50 for urging shuttle needle 20 out of the opening 54 of needle housing 16 and a snare 40 for engaging the proximal end of shuttle needle 20 to guide shuttle needle 20 at various stages of the suturing operation, such as through to the proximal side 102 of tissue, back into the needle housing 16 and into the desired position within needle housing 16.

In the embodiment of shuttle needle 20 shown in FIGS. 2B and 2C, the needle 20 includes opposing dual puncturing points 22 and 24 and, in the embodiment shown, opposing engagement surfaces. The first or distal end of shuttle needle 20 includes puncturing point 22, which transitions to a first engagement surface formed by shoulder 36 and narrowed distal neck area 26. Shuttle needle 20 includes at its opposite, proximal end, a proximal puncturing point 24, which transitions to a second engagement surface formed by shoulder 38 and narrowed proximal neck area 28.

In the embodiment of shuttle needle 20 shown in FIG. 2A, the distal end of needle 20 is not pointed and may be rounded or flat. The proximal end of shuttle needle 20 includes a first, or proximal puncturing point 24. Opposing engagement surfaces are shown at each of the distal and proximal ends of shuttle needle 20 as described above. The first engagement surface is formed by shoulder 36 and narrowed distal neck area 26. The second engagement surface is formed by shoulder 38 and narrowed proximal neck area 28.

In the center body portion 48 of shuttle needle 20 is the eye 46 of the needle, or a similar structure through which a length of suture material 70 extends, generally from both sides of the eye 46 such that a double strand of suture is used in each stitch. The eye 46 is crimped closed during manufacture to lock the suture securely in the shuttle needle 20. Those skilled in the art will appreciate that any suitable structure for attaching a length of suture material to the needle 20 will suffice. Examples include, without limitation, the eye 46, slots, hooks, sleeves and similar structures for attaching the suture material to the needle 20.

In an alternative embodiment of channel member 12, the distal end 14 of channel member 12 may be open, as shown in FIG. 2B, to allow the distal puncturing point 22 of shuttle needle 20 to extend therefrom to effect puncturing of tissue for channel member 12 in lieu of puncturing with the point 18. In this embodiment, the diameter of the opening at the distal end of channel member 12 would be about the same or less that the greatest diameter of puncturing point 22 to prevent shuttle needle 20 from exiting the channel member 12 at the open distal end and to keep the channel member as clear as possible.

Fork member 30 includes a pair of tines 32 at the distal end of fork member 30 and either one or two elongate rods 34 that extend in the proximal direction and are movable axially back and forth (or, distally and proximally relative, in use, to the practitioner) within the length of channel member 20. A single rod 34 may split into two rods to lead to the pair of tines 32 at any suitable location along its length. Dual rods 34 may alternatively be provided which lead in parallel, for example, to the tines 32, which bends upwardly to engage each side of the engagement surface at distal neck 26 of shuttle needle 20. When fork member 30 is moved distally, tines 32 push against distal shoulder 36 to move shuttle needle 20 distally with the fork member 30. When fork member 30 is moved proximally within channel member 12, tines 32 contact body portion 48 of shuttle needle 20 and push the shuttle needle 20 proximally with the fork member 30.

Ramp member 50, in the embodiment shown, is an elongate bar or rail having a ramp slope 52 at the distal end thereof. Ramp member 50 is movable axially, back and forth (or, distally and proximally relative, in use, to the practitioner) within the length of channel member 20. Ramp member 50 is slightly smaller in width than the diameter of the channel member 20 to allow unhindered axial movement within channel member 20, but to inhibit rotational movement or twisting within channel member 20. Alternatively, or in addition, ramp member 50 may be guided axially by a track member (not shown) running along at least a portion of the floor 56 and/or a portion of the ceiling of channel member 20.

Ramp member 50 is operatively connected, by any suitable known manner, or integrally connected, to a push rod 76, which is preferably biased in the distal direction, but locked against the complete advance of ramp member 50 in the distal direction by a locking mechanism 82 in body 60. Ramp member 50 advances distally in a limited, or first stage of distal progression upon actuation of push rod 76 in body 60 of apparatus 10, as shown in FIG. 14, and, advances distally in a more rapid, second stage of progression to urge at least the proximal end of shuttle needle 20 out of needle housing 16 upon release of locking mechanism 82, as explained more fully below.

Figure 14A:
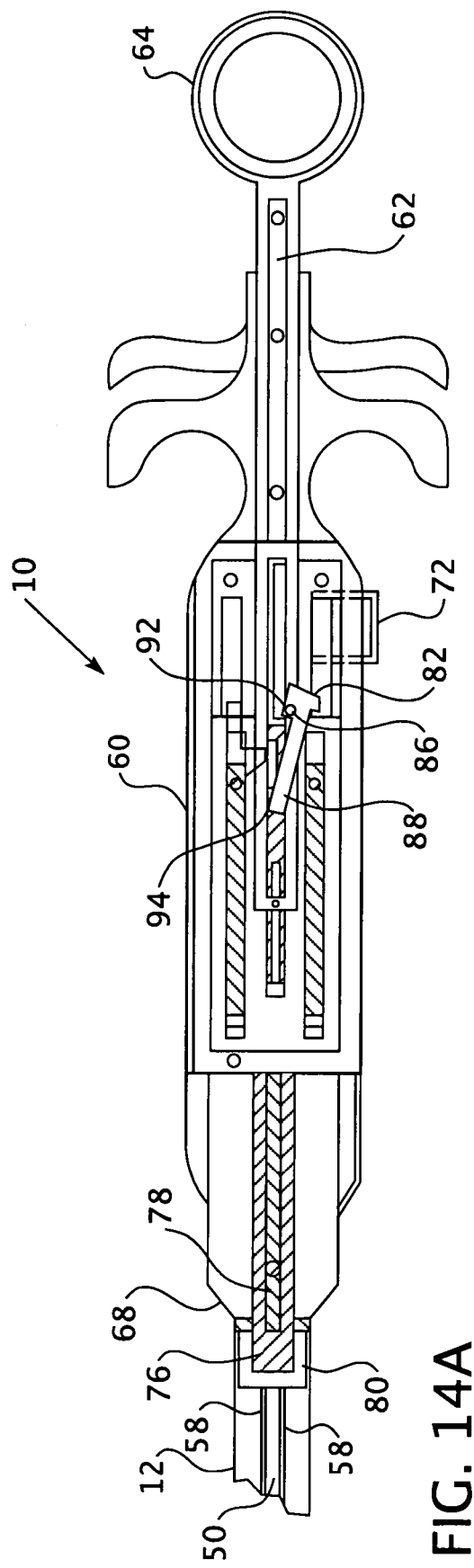
FIGS. 14A and B are section views of the actuation mechanism of the suturing apparatus of the present invention in two stages of operation.
Figure 14B:
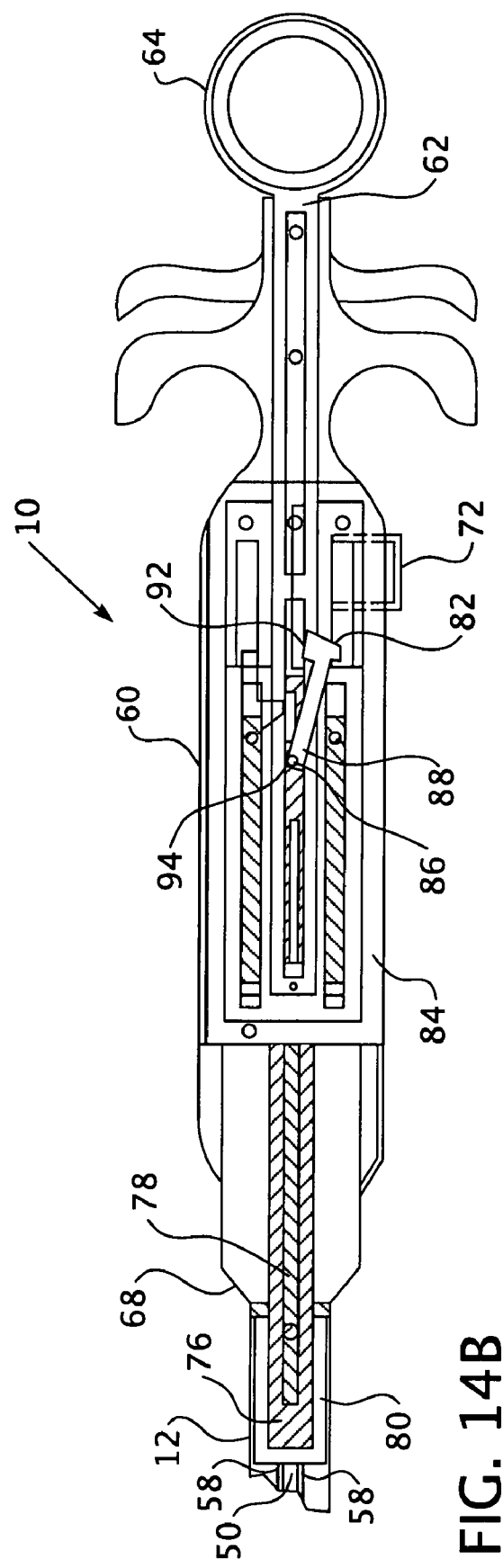
Figure 15:
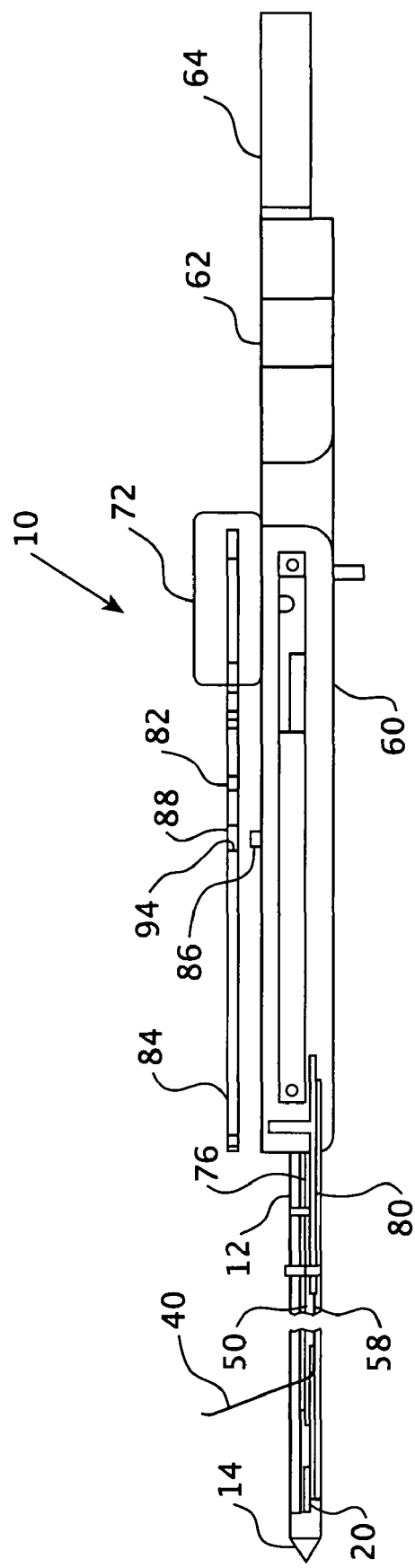
FIG. 15 is a side section view of the actuation mechanism of FIGS. 14A and B.

Referring to FIGS. 14A, B and 15, push rod 76 has a pin 86 positioned at an intermediate location on one surface of the rod 76. The locking mechanism 82 includes a plate 84 having a track 88 to capture pin 86, and thereby limits the full progression of push rod 76. Push rod 76 can be moved axially by pushing or pulling rod 62. As shown in FIGS. 14A and B, when rod 62 is pushed in the distal direction, movement of rod 62 causes some axial movement of rod 76 in the distal direction. Pin 86 is carried by the movement of rod 76 from the stop section 92 to track 88 of locking mechanism 82. Track 88 is configured to allow pin 86 of push rod 76 to move in the proximal direction until pin 86 reaches stop notch 92, and in the distal direction until pin 86 reaches stop notch 94, thereby locking push rod 76 against further distal movement until button 72, or any suitable actuation device, actuates a lever that raises and lowers plate 84. As shown in FIG. 15, by raising plate 84, the track 88 is lifted away from pin 86, thereby releasing push rod 76. Because push rod 76 is biased in the distal direction, upon release of pin 86 from track 88, push rod 76 advances in the distal direction rapidly, thereby pushing ramp member 50 rapidly toward shuttle needle 20 and urging the proximal end of shuttle needle 20 upwards at an angle (about the angle of the ramp slope 52) and out of the opening 54 of needle housing 16.

As shown in FIG. 3, when ramp member 50 is advanced distally while shuttle needle 20 is positioned within needle housing 16 with the body portion 48 and the proximal puncturing point 24 positioned beneath opening 54, ramp slope 52 slides under proximal puncturing point 24 to urge body portion 48 and the proximal end of shuttle needle 20 upwards, at an angle, out of opening 54. The distal end of shuttle needle 20 is held in place initially by tines 32 and the edge of channel member 12 at the distal end of opening 54.

Snare 40 is formed of wires 58 which extend along the length of channel member 12 to form a loop portion 44 and a noose 42 at the distal end of the snare 40. The proximal ends of wires 58 are operatively connected to, or integrally connected to, an actuation rod 80 in the body 60 of suturing apparatus 10. The noose 42 of snare 40 is configured to grab and hold the proximal neck 28 of shuttle needle 20 at a stage of the suturing operation, as described more fully below. The loop 44 of snare 40 is compressed within channel member 12 for certain stages of the suturing operation, when, as shown for example, in FIGS. 7-9, snare 40 is pulled in the proximal direction (for example, by pulling actuation rod 80 of apparatus body 60, or a similar member operatively connected to snare 40, in the proximal direction as shown in FIG. 14) such that that loop 44 is pulled into channel member 12 proximal to opening 54.

In use, suturing apparatus 10 may be used, for example, with an endoscope. The apparatus 10 of the present invention may also be used in a NOTES procedure. Those skilled in the art will recognize that the suturing apparatus 10 of the present invention may also be used in open surgery where the distal side 100 of tissue to be sutured is not readily accessible to the practitioner and a tool is deemed appropriate to facilitate such access.

When used with an endoscope, the distal end of channel member 12 would be inserted into the proximal end of a working channel of an endoscope to guide channel member 12 to an internal site of a patient undergoing a procedure requiring sutures at or near the internal site. The distal end of channel member 12 would be advanced to the distal end of the working channel of the endoscope and would exit the working channel and advance to the internal site to be sutured. Push rods 76, 78 and 80 may be operatively connected or linked to handle rod 62 such that all three advance at least some distance along their total possible paths when handle 62 is pushed in the distal direction. Thus, when the surgeon, or other practitioner, pushes handle 62 of apparatus 10 distally, the distal movement of the handle 62 drives fork member 30 distally, which in turn drives shuttle needle 20 distally to the desired position at the distal end of channel member 12, in position for the tissue puncture at the first puncture site selected by the surgeon. Similarly, the snare 40 is advanced such that, as the channel member 12 approaches the tissue, the noose 42 of snare 40 is positioned proximal to proximal neck 28 of shuttle needle 20, within the channel member as shown in FIG. 2B. Ramp member 50 moves distally as well in its first stage of distal progression to push shuttle needle 20 close to the distal end of channel member 12. The first puncture site may be an existing puncture site or may be the initial puncture site in a procedure, such as a stomach reduction.

Figure 10:
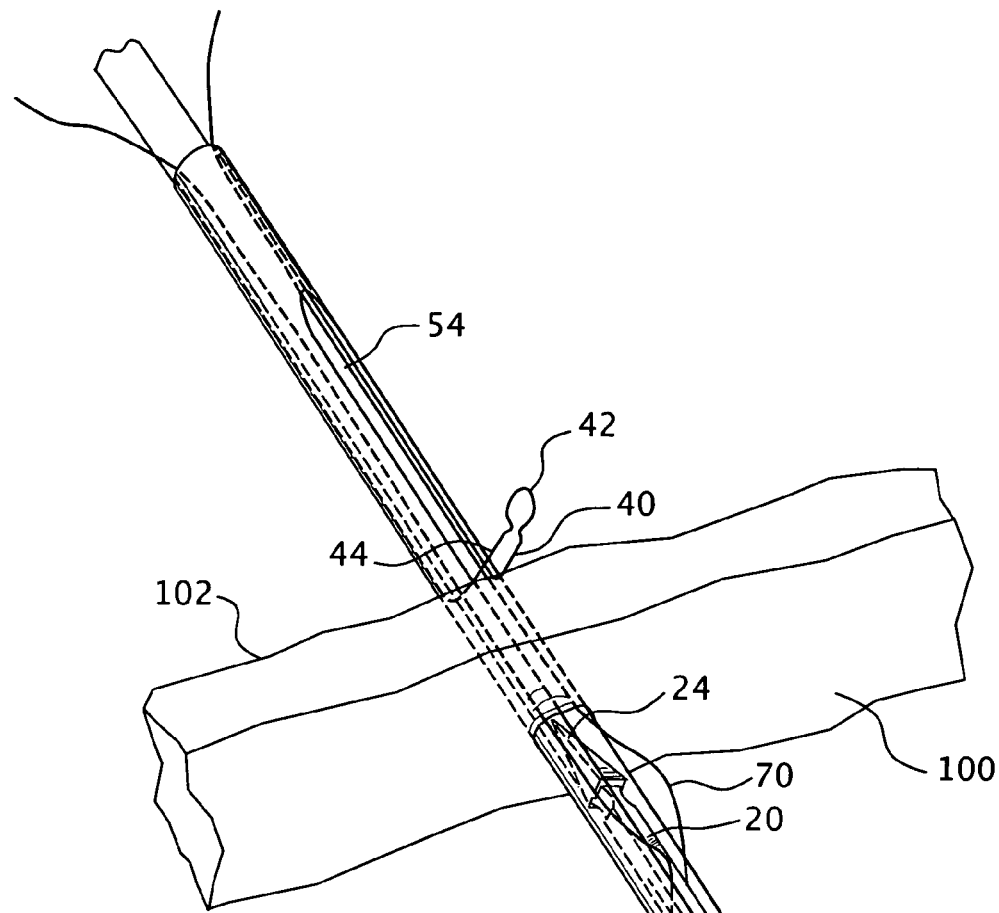
FIG. 10 is a view of the channel member and needle after passing from the proximal to the distal side of the tissue.

A trigger on body 60 or on handle 62 of apparatus 10 is pushed to advance snare 40 to position loop 44 beneath opening 54 so that it is free to pop out of opening 54, as shown in FIGS. 2C and 3. In one method of suturing tissue, the channel member 12 may be passed through the tissue. As the channel member 12 and shuttle needle 20 pass through the tissue, the snare 40 does not pass through the tissue, but extends out of channel member 12 on the proximal side 102 of the tissue and may rest on the tissue, as shown in FIG. 10, optionally providing some stabilization for the tissue being punctured. Referring to FIG. 10, the tip 18 of channel member 12 punctures the tissue at a first puncture site, passing from the proximal side 102 to the distal side 100 of the tissue. In the alternative embodiment described above and shown in FIG. 2B, the distal puncturing point 22 of shuttle needle 20 would be exposed through the open distal end of channel member 12 to puncture the tissue 102/100.

The channel member 12 is passed far enough through the tissue to pass shuttle needle 20 through to the distal side of the tissue. The suture material 70 attached to the eye 46 of shuttle needle 20 passes to the distal side of the tissue with the shuttle needle 20. At this stage of the suturing operation, the shuttle needle 20 is positioned within needle housing 16, with tines 32 of fork member 30 engaging the distal neck 26. Ramp member 50 is spaced axially from shuttle needle 20 and loop 44 and noose 42 of snare 40 are outside of channel member 12.

The fork member 30 pulls the shuttle needle 20 back in the proximal direction to position all but the distal end and neck of shuttle needle 20 beneath opening 54. To create the back stitch (i.e., to pull the suture material through to the proximal side of the tissue at a second puncture site spaced from the first puncture site), the locking mechanism 82 is released, as described above, to allow ramp member 50 to rapidly advance distally in its second stage of progression, contact the shuttle needle 20 and urge shuttle needle 20 upwardly at an angle, as shown in FIG. 3, in a barbed, harpoon-like configuration relative to channel member 12.

Figure 11:
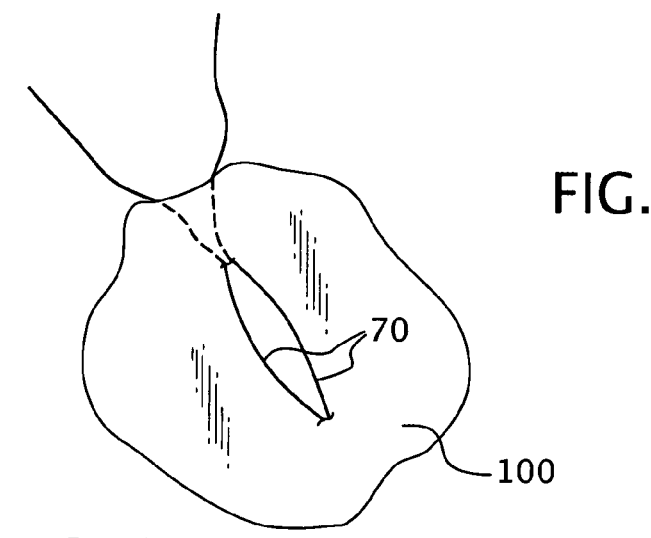
FIG. 11 is a view of the stitch that would be provided by a single stitch sequence through the tissue.

At this stage, channel member 12 is pulled in the proximal direction, pulling the proximal puncturing point 24 of shuttle needle 20 with it. However, channel member 12 will pass back through the first puncture site, while the proximal puncturing point 24 of shuttle needle 20 will be pulled, still at an angle, proximally through a second puncture site, moving from the distal side of the tissue 100 to the proximal side of the tissue 102 and leading the suture material 70 proximally with it to create a stitch, as shown in FIG. 11. As the proximal puncturing point 24 of shuttle needle 20 punctures the tissue, the distal end of shuttle needle 20 is securely held in the distal end of channel member 12 by tines 32.

Figure 6:
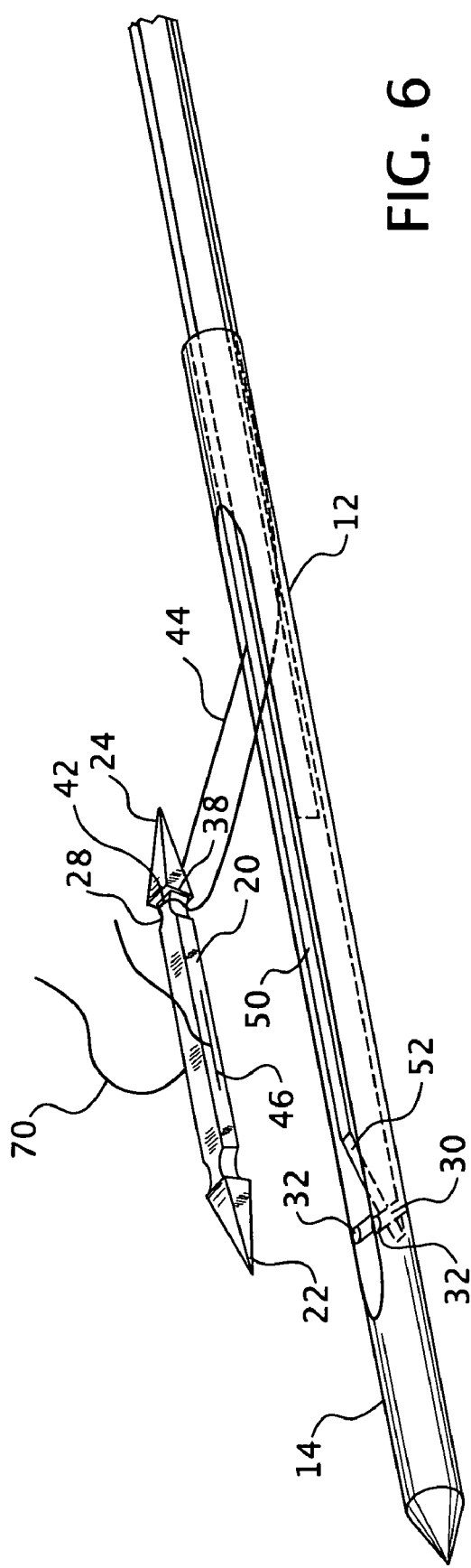
FIG. 6 is a partial view of the channel member showing the snare pulling the needle proximally through tissue.

Before the distal end of channel member 12 can be moved completely back to the proximal side of the tissue 102, however, the shuttle needle 20 has to be completely removed from the needle housing 16. Referring to the sequence shown in FIGS. 4-6, when the proximal puncturing point 24 of shuttle needle 20 is on the proximal side of the tissue 102, noose 42 is lowered onto, and grabs the second engagement surface at the proximal neck 28 of shuttle needle 20. (FIG. 4) When shuttle needle 20 is securely within the noose 42 of snare 40, fork member 30 is pulled in the proximal direction, releasing the distal neck and shoulders 26, 36 of shuttle needle 20, (FIG. 4) allowing snare 40 to pull shuttle needle 20 completely out of needle housing 16 (FIG. 5). When free of shuttle needle 20, channel member 12 is free to be completely drawn back to the proximal side of the tissue 102 through the first puncture site (FIG. 6). Snare 40 moves with channel member 12 in the proximal direction, pulling shuttle needle 20 completely through the second puncture site of the tissue.

Figure 7:
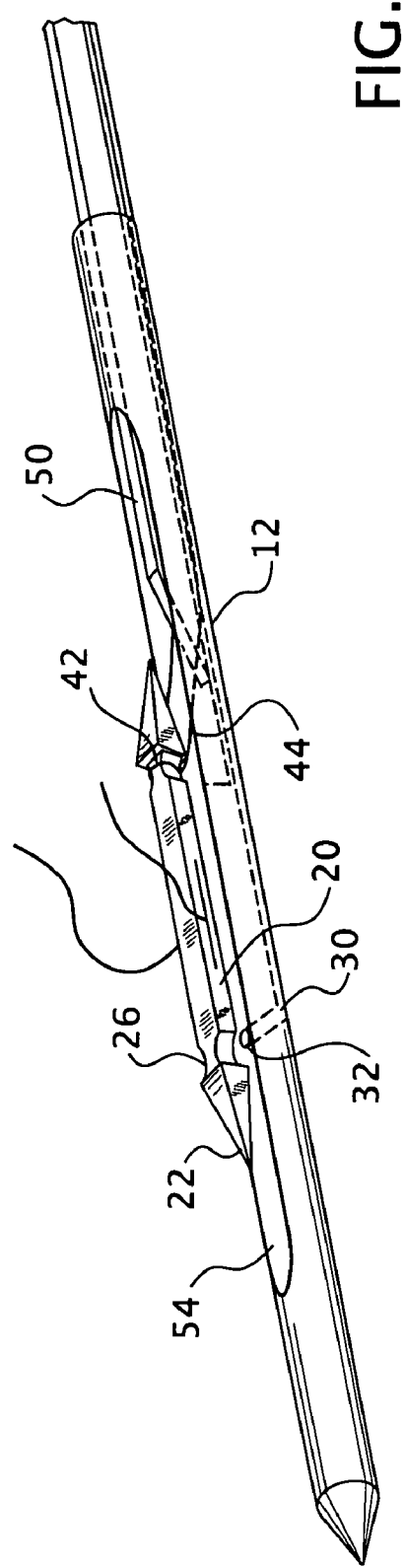
FIG. 7 is a partial view of the channel member showing the snare lowering the needle back into the needle housing.

In the next stage of the suturing procedure as shown in FIG. 7, snare 40 lowers shuttle needle 20 back into the needle housing 16 through opening 54. Prior to or simultaneously during this stage, ramp member 50 is pulled in the proximal direction, to clear the needle housing for the return of shuttle needle 20. Snare 40 is pulled in the proximal direction by pulling the rod 62, and thereby rod 80 to which snare wires 58 are directly or operatively attached, in the proximal direction. Ramp member 50 is pulled proximally and lock mechanism 82 is re-engaged by lowering plate 84 and with it, notch 88. As shown in FIG. 8, the shuttle needle 20 is pulled into needle housing 16 and the tines 32 of fork member 30 re-engage the distal neck 26 of shuttle needle 20. As shown in FIG. 9, fork member 30 and snare 40 push shuttle needle 20 in the distal direction within channel member 12, back toward the distal end thereof in position to begin another stitch through the tissue in the distal direction. The process is repeated until the desired number of stitches has been made.

Figure 12:
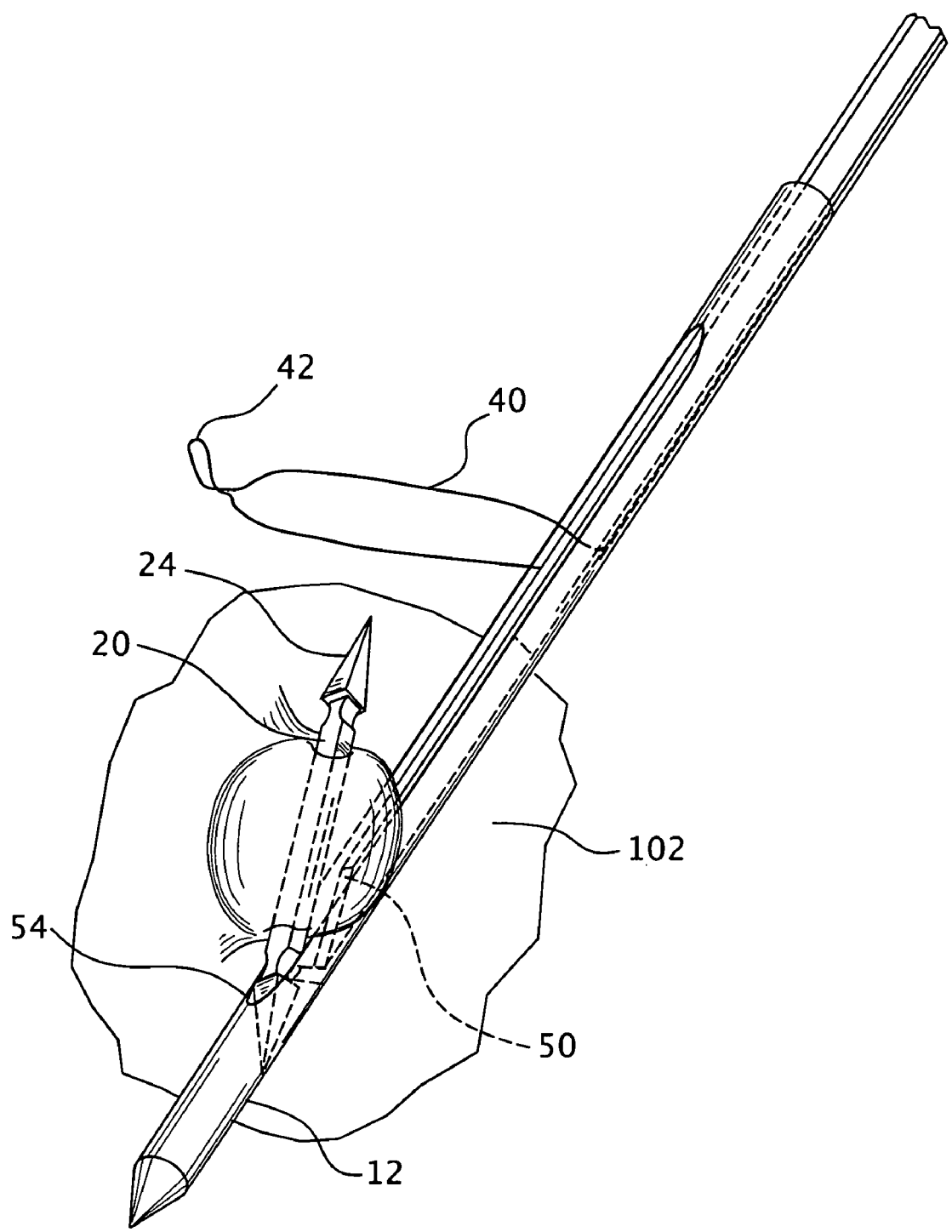
FIG. 12 is a view demonstrating a suturing technique wherein tissue is punctured only with the needle and not with the channel member.

Alternatively, the suturing can take place by passing only the shuttle needle 20 through tissue while keeping the channel member 12 on the proximal side 102 of the tissue. Referring to FIG. 12, the tissue is punctured by passing the proximal tip 24 of shuttle needle 20 through a section of tissue. The same procedure for lifting the needle 20 out of the needle housing 16 through opening 54 is carried out, as shown in FIG. 3. The needle 20 is pulled by pulling the channel member 12 while the needle 20 is still held by tines 32 to advance the tip 24 through the desired section of tissue. Needle 20 is further advanced and pulled through the tissue by the procedure shown and described with reference to FIGS. 4-6 above, then lowered back into needle housing 16 as shown in FIG. 7. The process is repeated until the desired number of stitches has been made.

Figure 13:
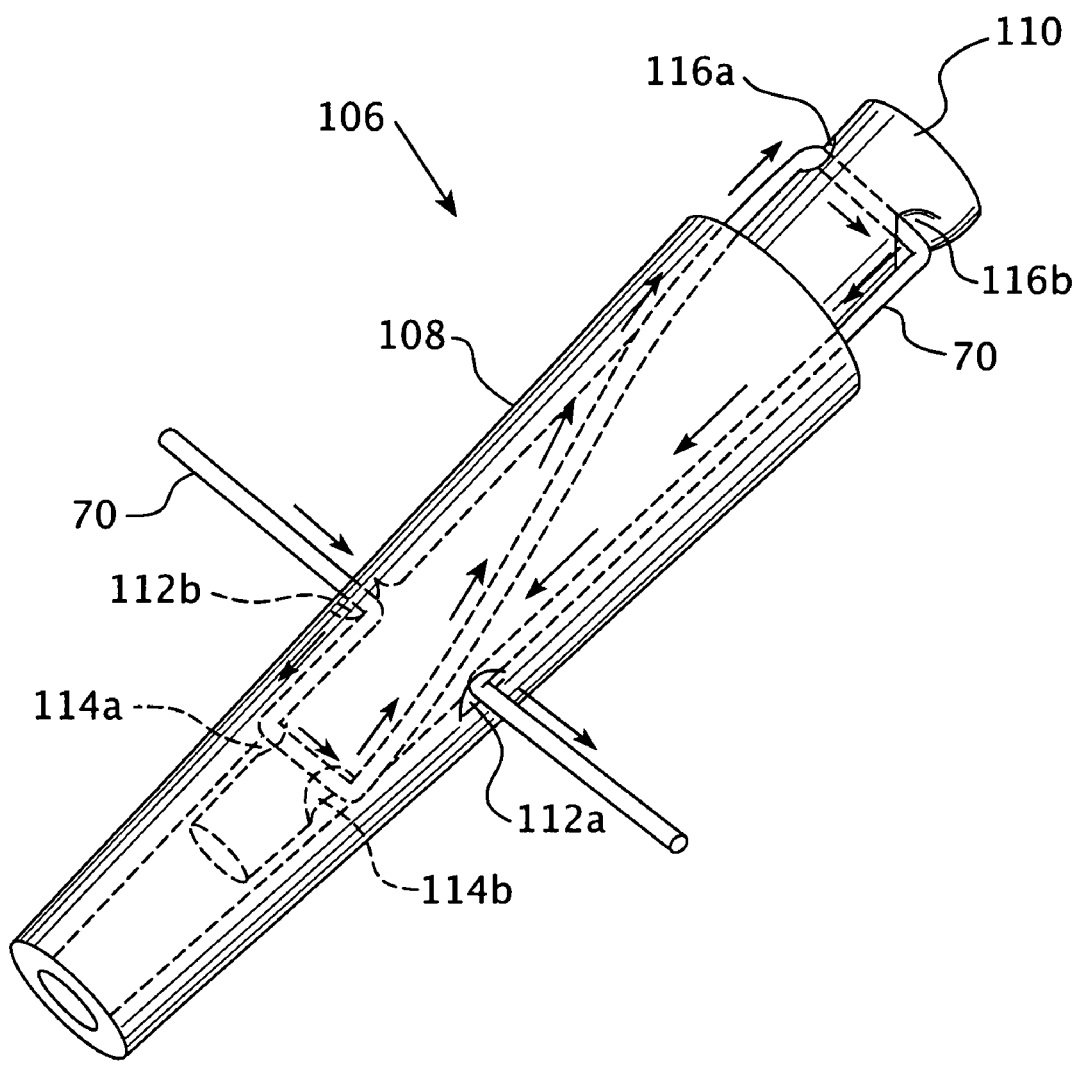
FIG. 13 is a view of an embodiment of a suture anchor attached to a length of suture.

Another tool would be used to tie off, or knot the suture ends before cutting the suture from shuttle needle 20 to complete the suturing procedure. A suture anchor, or suture tag having co-axial inner and outer cylinders axially movable relative to each other, may be provided. The outer cylinder of one embodiment of such a suture anchor may have a tapered inner surface and the inner cylinder may have a tapered outer surface for complementary locking engagement with the tapered inner surface of the outer cylinder to lock the suture material in a desired position. As shown in FIG. 13, a suture anchor or tag 106 having an outer tapered cylinder 108 and a co-axial inner tapered cylinder 110, positioned within outer tapered cylinder 108, can be used to tie off one or both ends of the suture. The suture 70 is directed through three passages 112, 114 and 116. The suture tags 106 are configured for attachment at one or both of the ends of the length of suture 70 for securing the suture 70 to the tissue at the start of and/or the completion of suturing.

Referring to FIG. 13, the suture tag 106 may be tied to the suture by drawing the suture 70 through passage entrance 112b in outer tapered cylinder 108, then through passage entrance 114a of inner tapered cylinder 110, out through passage exit 114b and over the surface of inner cylinder 110 to the wider end thereof and into passage entrance 116a, out of passage exit 116b and between the two cylinders 108, 110 to passage exit 112a. When the side of suture tag 106 having passage 112a, for example, is adjacent the tissue, by pulling on the opposite portion of suture 70, in this case, the portion that extends from passage 112b, the inner tapered cylinder 110 is pulled out of the outer tapered cylinder 108 allowing the suture to be pulled through until the tissue to be ligated is compressed to the desired degree. By applying a tension force on the portion of suture 70 that extends from the passage at 112a, tapered cylinder 110 is pulled into the outer cylinder 108, wedging itself against the narrowing taper on the inside surface of outer cylinder 108, and locking the suture 70 to stop any further slipping or sliding movement of the suture through the passages 112, 114 116. As long as the tension of the portion of suture 70 extending from passage 112a is greater than the tension applied to the portion of suture 70 extending from passage 112b, no sliding of the suture 70 will occur, thus providing a one way suture lock. Any suitable means of tying the suture or attaching it to the suture tag 106 will suffice.

The suture tag 106 may be applied to the suture 70 in a separate step after the forgoing suturing procedure with the suturing apparatus is completed or, it may be placed on the trailing end of the suture 70 and used to cinch suture 70 when the shuttle needle 20 is itself used as a distal suture tag. The suture tag 106 may also be used to cinch both ends of the same suture 70, previously placed in tissue by transferring the suture 70 thru the one-way suture tag 106 using a loop type snare, which is formed by a loop of stiff fiber that is feed through the needle eye. The suture tag 106 may have such a loop pre-installed to allow the surgeon or clinician to place the suture tag 106 onto suture 70 by placing both strands in the loop of the loop type snare and pulling the loop through the tag 106 to drag the suture through the tag 106.

Instead of a suture tag 106, the shuttle needle 20 alone may be used as a tag and left at the end of the stitching to function as an anchor to secure the stitching.

The devices disclosed herein may be made of stainless steel, titanium or any biocompatible material or bioabsorbable material. The suture materials used with the suturing apparatus and suture tags are also made of biocompatible or bioabsorbable materials. The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the various embodiments of the invention described herein will be processed before patient use. First, a new or used instrument, in this case, the suturing apparatus 10 is obtained and if necessary cleaned. The suturing apparatus 10 can then be sterilized by any suitable known sterilization technique. This can be done by any number of ways known to those skilled in the art including beta or gamma radiation, ethylene oxide, steam. In one sterilization technique, the suturing apparatus 10 is placed in a closed and sealed container, such as a plastic or TYVEK bag. The container and instruments are then placed in a field of radiation that can penetrate the container, such as gamma radiation, x-rays, or high-energy electrons. The radiation kills bacteria on the instruments and in the container. The sterilized instruments can then be stored in the sterile container. The sealed container keeps the deployment device and anchors sterile until it is opened in the medical facility.

In summary, numerous benefits are apparent which result from employing the concepts of the invention. The foregoing description of one or more embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be limited only by the claims appended hereto.

The invention claimed is:

1. A surgical suturing apparatus comprising:
   a channel having a longitudinal axis, a distal end and a proximal end, said channel defining a housing at the distal end thereof having an opening therein;
   a needle releasably disposed within said housing, said needle having a distal end, a proximal end, and a proximal puncturing point at the proximal end, said needle being structured for attachment to a length of suture material;
   a needle positioning assembly having members movable relative to said channel for effecting a desired number of release and retrieval cycles for releasing said needle from said housing and guiding the return of said needle to said housing; and
   an actuation assembly for controlling said members of said needle positioning assembly;
   wherein needle positioning assembly comprises (a) an engagement member configured for releasably engaging said needle to effect axial movement of said needle within said channel; (b) a ramp member movable axially within said channel and configured for operative contact with said needle for effecting movement of said needle to a first stage of progression adjacent said opening of said housing and to a second stage of progression wherein at least said proximal puncturing point is out of said housing; and (c) a movable snare member having a portion configured for engagement with said needle for guiding said needle when said needle is out of said housing.

2. The surgical suturing apparatus recited in claim 1 wherein said actuation assembly further comprises:
a body portion;
a handle;
a plurality of rods operatively connected to said members of said positioning assembly for controlling movement of said needle.

3. The surgical suturing apparatus recited in claim 1 wherein the channel forms a distal puncturing point at the distal end thereof, and the suturing apparatus further comprises a length of suture material attached to said needle such that the puncture of tissue with said distal puncturing point and movement of said needle through said tissue in a first direction threads said suture material through said tissue in the first direction.

4. The surgical suturing apparatus recited in claim 3 wherein the puncture of tissue with said proximal puncturing point and movement of said needle through said tissue in a second direction threads said suture material through said tissue in the second direction.

5. The surgical suturing apparatus recited in claim 1 wherein said distal end of said needle forms a distal puncturing point and said channel is open at the distal end thereof to expose said distal puncturing point for puncturing tissue in a first direction when said channel is moved in said first direction.

6. The surgical suturing apparatus recited in claim 1 wherein said needle has a first engagement surface adjacent said distal end and a second engagement surface adjacent said proximal puncturing point.

7. The surgical suturing apparatus recited in claim 6 wherein said portion of said snare member further comprises:
a noose for engagement with said second engagement surface of said needle;
an expandable loop proximal to said noose, said loop being biased away from the longitudinal axis of said channel; and
an elongate section proximal to said loop and operatively connected to said actuation assembly, wherein movement of said elongate section in a distal direction positions said noose and loop adjacent said opening of said housing to enable the release of said loop and noose from said channel and movement in a proximal direction when said noose and loop are out of said channel effects the return of said loop and said noose to said channel.

8. The surgical suturing apparatus recited in claim 6 wherein said ramp member comprises:
a rail operatively connected to said actuation assembly at a proximal end of said rail; and,
a slope at a distal end of said rail for contact with said needle.

9. The surgical suturing apparatus recited in claim 8 wherein said slope, when moved into the second stage of progression, urges said needle from said housing at an angle to position said proximal puncturing point at a desired location for puncturing tissue.

10. The surgical suturing apparatus recited in claim 6 wherein said engagement member comprises an elongate portion operatively connected to said actuation assembly and a pair of tines for engaging said needle at said first engagement surface.

11. The surgical suturing apparatus recited in claim 1 wherein said actuation assembly further comprises:
a body portion;
a handle;
a first push rod housed in said body portion and being operatively connected to said handle and said engagement member for driving axial movement of said engagement member;
a second push rod housed in said body portion and being operatively connected to said handle and said ramp member for driving axial movement of said ramp member to said first stage of progression and for driving movement of said ramp member in said second stage of progression;
a lock mechanism for locking said second push rod against movement of said ramp member to said second stage of progression;
a release mechanism for selectively unlocking said second push rod to trigger movement of said ramp member to said second stage of progression; and
a third push rod housed in said body portion and being operatively connected to said handle and said snare member for driving axial movement of said snare member to a position for release of said portion of said snare from said channel and for return of said portion to said channel.

12. The surgical suturing apparatus recited in claim 11 wherein movement of said third push rod in a distal direction positions said portion of said snare member within an opening in said housing to effect the release of said portion of said snare member for engagement with said needle, and movement of said third push rod in a proximal direction when said portion engages said needle effects (i) the proximal travel of said needle when said needle is out of said housing to pull said needle through tissue in said proximal direction and (ii) the return of said portion of said snare member and said needle to said channel.

13. The surgical suturing apparatus recited in claim 12 wherein said actuation assembly further comprises a trigger for moving said snare portion distally to said opening in said housing.

14. The surgical suturing apparatus recited in claim 11 wherein said lock mechanism comprises a pin extending outwardly from said second push rod, and a locking plate having a notch therein for stopping said pin against movement in a distal direction beyond said notch.

15. The surgical suturing apparatus recited in claim 14 wherein said release mechanism comprises a lever for lifting said locking plate to release said pin from said notch.

16. The surgical suturing apparatus recited in claim 1 further comprising at least one suture tag, each having passages therethrough for attachment to the suture material, said suture tags being configured for attachment at one or both ends of the length of suture for securing the suture to said tissue.

17. The surgical suturing apparatus recited in claim 16 wherein the suture tag comprises an outer tapered cylinder and an inner tapered cylinder within said outer cylinder, each said cylinder having at least one passage therethrough for passage of the suture material.

18. A surgical suturing apparatus comprising:
a channel having a longitudinal axis, a distal end and a proximal end, said channel defining a housing at the distal end thereof having an opening therein;
a needle releasably disposed within said housing, said needle having a first end and a first puncturing point at a second end, said needle being structured for attachment to a length of suture material;
a needle positioning assembly having members movable relative to said channel for effecting a desired number of release and retrieval cycles for releasing said needle from said housing and guiding the return of said needle to said housing, wherein needle positioning assembly comprises:
an engagement member configured for releasably engaging said needle to effect axial movement of said needle within said channel;
a ramp member movable axially within said channel and configured for operative contact with said needle for effecting movement of said needle to a first stage of progression adjacent said opening of said housing and to a second stage of progression wherein at least said first puncturing point is out of said housing; and
a movable snare member having a portion configured for engagement with said needle for guiding said needle when said needle is out of said housing; and
an actuation assembly for controlling said members of said needle positioning assembly.

19. The surgical suturing apparatus recited in claim 18 wherein said needle has a first engagement surface adjacent said first end and a second engagement surface adjacent said first puncturing point.

20. The surgical suturing apparatus recited in claim 19 wherein said portion of said snare member further comprises:
a noose for engagement with said second engagement surface of said needle;
an expandable loop proximal to said noose, said loop being biased away from the longitudinal axis of said channel; and
an elongate section proximal to said loop and operatively connected to said actuation assembly, wherein movement of said elongate section in a distal direction positions said noose and loop adjacent said opening of said housing to enable the release of said loop and noose from said channel and movement in a proximal direction when said noose and loop are out of said channel effects the return of said loop and said noose to said channel.

21. The surgical suturing apparatus recited in claim 19 wherein said ramp member comprises:
a rail operatively connected to said actuation assembly at a proximal end of said rail; and,
a slope at a distal end of said rail for contact with said needle.

22. The surgical suturing apparatus recited in claim 21 wherein said slope, when moved into the second stage of progression, urges said needle from said housing at an angle to position said first puncturing point at a desired location for puncturing tissue.

23. The surgical suturing apparatus recited in claim 19 wherein said engagement member comprises an elongate portion operatively connected to said actuation assembly and a pair of tines for engaging said needle at said first engagement surface.

24. The surgical suturing apparatus recited in claim 18 wherein said actuation assembly further comprises:
a body portion;
a handle;
a first push rod housed in said body portion and being operatively connected to said handle and said engagement member for driving axial movement of said engagement member;
a second push rod housed in said body portion and being operatively connected to said handle and said ramp member for driving axial movement of said ramp member to said first stage of progression and for driving movement of said ramp member in said second stage of progression;
a lock mechanism for locking said second push rod against movement of said ramp member to said second stage of progression;
a release mechanism for selectively unlocking said second push rod to trigger movement of said ramp member to said second stage of progression; and
a third push rod housed in said body portion and being operatively connected to said handle and said snare member for driving axial movement of said snare member to a position for release of said portion of said snare from said channel and for return of said portion to said channel.

25. The surgical suturing apparatus recited in claim 24 wherein movement of said third push rod in a distal direction positions said portion of said snare member within an opening in said housing to effect the release of said portion of said snare member for engagement with said needle, and movement of said third push rod in a proximal direction when said portion engages said needle effects (i) the proximal travel of said needle when said needle is out of said housing to pull said needle through tissue in said proximal direction and (ii) the return of said portion of said snare member and said needle to said channel.

26. The surgical suturing apparatus recited in claim 25 wherein said actuation assembly further comprises a trigger for moving said snare portion distally to said opening in said housing.

27. The surgical suturing apparatus recited in claim 24 wherein said lock mechanism comprises a pin extending outwardly from said second push rod, and a locking plate having a notch therein for stopping said pin against movement in a distal direction beyond said notch.

28. The surgical suturing apparatus recited in claim 27 wherein said release mechanism comprises a lever for lifting said locking plate to release said pin from said notch.

* * * * *